US008691983B2

(12) United States Patent
Wen et al.

(10) Patent No.: US 8,691,983 B2
(45) Date of Patent: Apr. 8, 2014

(54) BRUSH POLYMER COATING BY IN SITU POLYMERIZATION FROM PHOTOREACTIVE SURFACE

(75) Inventors: Jie Wen, Eden Prairie, MN (US); Laurie R. Lawin, New Brighton, MN (US); Patrick Guire, Hopkins, MN (US)

(73) Assignee: Innovative Surface Technologies, Inc., St. Paul, MN (US)

( * ) Notice: Subject to any disclaimer, the term of this patent is extended or adjusted under 35 U.S.C. 154(b) by 688 days.

(21) Appl. No.: 12/714,911

(22) Filed: Mar. 1, 2010

(65) Prior Publication Data

US 2010/0227077 A1 Sep. 9, 2010

Related U.S. Application Data

(60) Provisional application No. 61/157,058, filed on Mar. 3, 2009.

(51) Int. Cl.
*A01N 43/66* (2006.01)
*A61K 31/53* (2006.01)
*C07D 251/00* (2006.01)

(52) U.S. Cl.
USPC .......................................... 544/221; 514/241

(58) Field of Classification Search
None
See application file for complete search history.

(56) References Cited

U.S. PATENT DOCUMENTS

| | | | |
|---|---|---|---|
| 3,580,927 A | 5/1971 | Wear | |
| 3,959,078 A | 5/1976 | Guire | |
| 4,043,331 A | 8/1977 | Martin et al. | |
| 4,605,413 A | 8/1986 | Urry et al. | |
| 4,722,906 A | 2/1988 | Guire | |
| 4,731,080 A | 3/1988 | Galin | |
| 4,973,493 A | 11/1990 | Guire | |
| 5,002,582 A | 3/1991 | Guire et al. | |
| 5,202,361 A | 4/1993 | Zimmerman et al. | |
| 5,258,041 A | 11/1993 | Guire et al. | |
| 5,331,027 A | 7/1994 | Whitbourne | |
| 5,414,075 A | 5/1995 | Swan | |
| 5,522,879 A | 6/1996 | Scopelioanos | |
| 5,563,056 A | 10/1996 | Swan et al. | |
| 5,637,460 A | 6/1997 | Swan et al. | |
| 5,714,360 A | 2/1998 | Swan et al. | |
| 5,741,551 A | 4/1998 | Guire et al. | |
| 5,942,555 A | 8/1999 | Swanson et al. | |
| 6,077,698 A | 6/2000 | Swan et al. | |
| 6,096,070 A | 8/2000 | Ragheb et al. | |
| 6,096,369 A | 8/2000 | Anders et al. | |
| 6,278,018 B1 | 8/2001 | Swan | |
| 6,391,948 B1 | 5/2002 | Clark et al. | |
| 6,683,126 B2 | 1/2004 | Keller et al. | |
| 6,811,856 B2 | 11/2004 | Nun et al. | |
| 6,852,389 B2 | 2/2005 | Nun et al. | |
| 6,858,284 B2 | 2/2005 | Nun et al. | |
| 7,211,313 B2 | 5/2007 | Nun et al. | |
| 7,348,055 B2 | 3/2008 | Chappa et al. | |
| 7,772,393 B2 | 8/2010 | Guire et al. | |
| 7,879,444 B2 | 2/2011 | Jiang et al. | |
| 2002/0004140 A1 | 1/2002 | Swan et al. | |
| 2002/0016433 A1 | 2/2002 | Keller et al. | |
| 2002/0150724 A1 | 10/2002 | Nun et al. | |
| 2003/0215649 A1 | 11/2003 | Jelle | |
| 2004/0162609 A1 | 8/2004 | Hossainy et al. | |
| 2004/0234487 A1 | 11/2004 | Bremser et al. | |
| 2005/0003203 A1 | 1/2005 | Brown | |
| 2005/0095695 A1 | 5/2005 | Shindler et al. | |
| 2005/0181015 A1 | 8/2005 | Zhong | |
| 2006/0030669 A1 | 2/2006 | Taton et al. | |
| 2006/0286305 A1 | 12/2006 | Thies et al. | |
| 2007/0003707 A1 | 1/2007 | Guire et al. | |

(Continued)

FOREIGN PATENT DOCUMENTS

| | | |
|---|---|---|
| EP | 187126 | 11/2007 |
| JP | 57-042742 | 3/1982 |
| JP | 57-117564 | 7/1982 |
| JP | 59-043061 | 3/1984 |
| WO | 93/16131 | 8/1993 |
| WO | 93/16176 | 8/1993 |
| WO | 97/07161 | 2/1997 |
| WO | WO 98/03489 | 1/1998 |
| WO | WO 99/15917 | 4/1999 |
| WO | WO 01/17575 | 3/2001 |
| WO | WO 01/21326 | 3/2001 |
| WO | 01/26702 | 4/2001 |
| WO | WO 01/40367 | 6/2001 |
| WO | 03/025267 | 8/2002 |
| WO | 03/030879 | 4/2003 |

(Continued)

OTHER PUBLICATIONS

International Search Report PCT/US2010/025838 dated Nov. 16, 2010 (3 pgs.).

Allen, et al., Photochemistry and Photopolymerization Activity of Novel 4-Alkylamino Benzophenone Initiators-Synthesis, Characterization, Spectroscopic and Photopolymerization Activity, European Polymer Journal, Pergamon Press, Ltd. Oxford, GB, vol. 26, No. 12, 1990, pp. 1345-1353, XP002393858.

(Continued)

*Primary Examiner* — James D Anderson
*Assistant Examiner* — Stephanie Springer
(74) *Attorney, Agent, or Firm* — Fulbright & Jaworski, LLP; Scott D. Rothenberger

(57) ABSTRACT

The invention provides compositions that include crosslinking agents having multiple photoactivatable groups, such as diaryl ketones, or a diaryl ketone, such as benzophenone, and at least one polymerizable monomer, such as a zwitterionic monomer. The compositions are useful as surface coating agents that provide brush type polymeric coatings. These polymeric coatings can be used on medical devices, such as artificial joints, to reduce wear and tear between the components of the joint and thus reduce or eliminate debris generated by friction between the joint components.

9 Claims, 2 Drawing Sheets

(56) References Cited

U.S. PATENT DOCUMENTS

| | | |
|---|---|---|
| 2007/0009657 A1 | 1/2007 | Zhang et al. |
| 2007/0281110 A1 | 12/2007 | Brown |
| 2008/0021126 A1 | 1/2008 | Dietliker et al. |
| 2008/0026662 A1 | 1/2008 | Ramsey |
| 2008/0268233 A1 | 10/2008 | Lawin et al. |
| 2010/0081750 A1 | 4/2010 | Guire et al. |
| 2010/0227077 A1 | 9/2010 | Wen et al. |
| 2010/0274012 A1 | 10/2010 | Guire et al. |
| 2011/0097277 A1 | 4/2011 | Jiang et al. |
| 2011/0282005 A1 | 11/2011 | Jiang et al. |

FOREIGN PATENT DOCUMENTS

| | | |
|---|---|---|
| WO | 03/097117 A1 | 11/2003 |
| WO | 2004/044281 | 5/2004 |
| WO | 2005/097223 | 10/2005 |
| WO | 2005/107455 | 11/2005 |
| WO | 2006/063181 | 6/2006 |
| WO | WO 2006/063181 | 6/2006 |
| WO | 2006/135910 | 12/2006 |
| WO | WO 2006/135910 | 12/2006 |
| WO | 2007/011731 | 1/2007 |
| WO | 2007/012050 | 1/2007 |
| WO | WO 2007/012050 | 1/2007 |
| WO | 2007/144356 | 12/2007 |
| WO | WO 2008023048 A2 * | 2/2008 |
| WO | 2008/106494 | 9/2008 |
| WO | 2009/002858 | 12/2008 |
| WO | 2009/002869 | 12/2008 |
| WO | 2010/028104 | 3/2010 |
| WO | 2010/033482 | 3/2010 |
| WO | 2010/101863 | 9/2010 |

OTHER PUBLICATIONS

Blawas, A.S., et al., Review: Protein Patterning, Biomaterials(19), p. 595-609 (1998).
Cao, X., et al., Photoimmobilization of biomolecules within a 3-dimensional hydrogel matrix, J. Biomater. Sci. Polymer Edn.(13), p. 623-636 (2002).
Chen, H., et al., Ultrafine Hydrogel Fibers with Dual Temperature- and pH-Responsive Swelling Behaviors, J. of Pol. Sci. A Pol. Chem,(42) p. 6331-6339 (2004).
Chua, K-N., et al., Stable immobilization of rat hepatocyte spheroids on galactosylated nanofiber scaffold, Biomaterials(26), p. 2537-2547 (2005).
Ellefson, S., et al., Surface Properties of Fused Salts and Glasses: I Sessile-Drop Method for Determining Surface Tension and Density of Viscous Liquids at High Temperatures, J. Am. Ceram. Soc. 21, 193-205, (1938).
Fang, J. et al., Applications of electrospun nanofibers, Chinese Science Bulletin(53), p. 2265-2286 (2008).
Geisman, C., et al., Photoreactive Functionalization of Poly(ethylene terephthalate) Track-Etched Pore Surf. w/"Smart" Polym Sys, Macromol. Chem. Phy. (206), p. 268-281 (2005).
Jin, Y., et al., Photocrosslinked Electrspun Chitosan-Based Biocompatible Nanofibers, J. of Applied Pol. Sci.(109), p. 3337-3343 (2008).
Kim, DJ, et al., Formationof Thermoresponsive Poly(N-isopropylacrylamide)/Dextran Particles by Atom Transfer Radical Polymerization, Macromol. Rapid Comm(24), p. 517-521 (2003).
Kim, S.H., et al., Reactive Electrospinnig of Cross-Linked Poly(2-hydroxyethylmethacrylate) Nanofibers and Elastic . . . , Macromolecules (38), p. 3719-3723 (2005).
Ko, Y-G., et al., Development of Rapid Cell Recovery System Using Temperature-Responsive Nanofiber Surfaces, Key Engineering Materials (342-343), p. 249-252 (2007).
Kroschwitz, ed. Plastics, Concise Encyclopedia of Polymer Science and Engineering, John Wiley & Sons, 1990, pp. 462-464.
Kubota, H., et al., Photografting of Acrylamine on Ethylene-Vinyl Alcohol Copolymer Film, Polymer International (34), p. 313-317 (1994).
Lalevee, J. et al., New Highly Efficient Radical Photoinitiators based on Si-Si Bond Cleavage, Macromolecules, 2007, American Chemical Society, 40, 8527-8530.
Li, D., et al., Electrospinning of Nanofibers: Reinventing the Wheel?, Adv. Mater.(16), p. 1151-1170 (2004).
Liu, H. et al., Ionic-Strength- and pH-Responsive Poly[acrylamied-co(maleic acid)] Hydrogel Nanofibers, Macromol. Chem. Phys. (208), p. 874-880 (2007).
Ma, Z., et al., Surface engineering of electrospun polyethylene terephthalate (PET) nanofibers towards development of a new material . . . , Biomaterials(26), pp. 2527-2536 (2005).
Ma, Z., et al., Potential of Nanofiber Matrix as Tissue-Engineering Scaffolds, Tissue Engineering(11), p. 101-109 (2005).
Mark, S., et al., Bioconjugation of Alk. Phosphatase to Mechanically Processed, Aq. Suspendible Electrospun Polym Nanofibers for Use . . . , Marcomol. Biosci.(8), p. 484-498 (2008).
Min, B.M. et al., Electrospinning of silk fibroin nanofibers and its effect on the adhesion and spreading of normal human keratinocytes . . . , Biomaterials(25), pp. 1289-1297 (2004).
Okuzaki, H., et al., Thermo-Responsive Nanfiber Mats, Macromolecules(42), p. 5916-5918 (2009).
Ramakrishna, S., et al., Electrospun nanofibers; solving global issues, Materials Toady (9), p. 40-50 (2006).
Roe, R.-J. et al., Polymers at Interfaces, J. Polym. Sci. C34 (1971) pp. 19-30.
Rothenberg, et al., Human and Rat Hepatocytes Cultured on Ultra-Web and Ultra-Web Polyamine Synth. Matrices show Enhanced Physiologic Activity, Application Note (4 pgs, 2008).
Rothenberger, et al., Rat Hepatocyte Culture Physiology Shows Enhanced Cytochrome P450 Activity on a Synthetic Extracellular Matrix, Cell Notes(20), p. 18-20 (2008).
Ryadnov, M.G., et al., Fiber Recruiting Peptides: Noncovalent Eecoration of an Engineered Protein Scaffold, J. Am. Chem. Soc. (126), p. 7454 (2004).
Ryong-Joon Roe, Surface Tension of Polymer Liquids, J. Phys. Chem. 72, pp. 2013-2017 (1968).
Ryong-Joon Roe et al., Interfacial Tension Between Polymer Liquids, J. Colloid Interface Sci. 31, (1969) pp. 228-235.
J. F. Padday in Surface and Colloid Science (edited by E. Matijevic)Wiley, N.Y. 1969, pp. 101-149.
R.-J. Roe, et al., Refinement of Pendent Drop Method for the Measurement of Surface Tension of Viscous Liquid, J. Phys. Chem. 71(1967) pp. 4190-4193.
Sanders, J., et al., Fibro-porous meshes made from polyurethane micro-fibers: effects of surface charge on tissue response, Biomaterials(26), p. 813-818 (2005).
Shengguag, C., et al., Synth. of pH-resp. crosslinked poly[styrene-co(maleic sodium anhydride)] and cellculose comp. hydrogel nanofibers . . . , Polym. Int(58) p. 545-551 (2009).
Ulbrict, M. et al., Ultrafiltration membrane surfaces with grafted polymer "tentacles": prep, char. and app. For covalent protein bonding, Biomaterials (19), pp. 1229-1237 (1998).
Yu, J., et al., Photocrosslinked Electrospun Chitosan-Based Biocompatible Nanofibers, J. of Applied Polym. Sci.,(109), p. 3337-3343 (2008).
Wu, S., Surface and Interfacial Tension of Polymer Melts, J. Phys. Chem 74, (1970), pp. 623-638.
Wu, S., Surface and Interfacial Tension of Polymer Melts, J. Colloid Interface Sci. 31, (1969), pp. 153-161.

* cited by examiner

Nylon-g-SBMAM (BP)

Nylon-g-SBMAM (Triazine Crosslinker of Example 1)

Uncoated Nylon

Left to right, Nylon-g-SBMAM (BP), Nylon-g-SBMAM (Triazine crosslinker of Example 1) and uncoated Nylon.

BRUSH POLYMER COATING BY IN SITU POLYMERIZATION FROM PHOTOREACTIVE SURFACE

CROSS REFERENCE TO RELATED APPLICATIONS

This application claims benefit of U.S. Provisional Application Ser. No. 61/157,058, filed on Mar. 3, 2009, entitled "Brush Polymer Coating by In Situ Polymerization From Photoreactive Surface", the contents of which are incorporated in their entirety herein by reference.

FIELD OF THE INVENTION

The invention relates generally to compositions that include cross linking agents that provide photoactivatable groups, such as aryl ketones, and at least one polymerizable monomer. Alternatively, the composition includes a diaryl ketone, such as benzophenone, and a polymerizable monomer, such as a zwitterionic monomer. The compositions are useful as surface coating agents that provide brush type polymeric coatings. These polymeric coatings can be used on medical devices, such as artificial joints, to reduce wear between the components of the joint and thus reduce or eliminate debris generated by friction between the joint components.

BACKGROUND OF THE INVENTION

There are several types of joints in the human body. These can be categorized into weight bearing and non-weight bearing joints. The hip, knee, ankle and intervertebral disc in the spine are considered load-bearing joints, while the finger and toe are considered non-weight bearing joints. The hip, knee, and ankle are further categorized as synovial joints, while the intervertebral disc is a cartilaginous joint. These joints, especially the weight bearing joints, can undergo degenerative changes due to disease, age, trauma, repetitive loading and/or genetics.

The individual whose joints experience such degeneration may incur significant discomfort, pain and even disability. Initially, the only option for the patient with degenerative changes to these joints was to undergo arthrodesis, or fusion, of the effected joint. Although this can effectively relieve pain and lead to an increase in the quality of life, fusion can significantly alter the normal biomechanical function of the effected joints. Treatment options have since advanced to include motion preserving implants, known as arthroplasty devices. These joint replacement devices usually comprise a pair of endplates with some type of intermediate components or articulating bearing surfaces to facilitate motion between the adjacent vertebral bodies.

One challenge for arthroplasty devices, whether for the hip, knee, ankle or spine, is the selection of the proper materials for the various components thereof. Biocompatibility—the suitability of a material for exposure to the body or bodily fluids—and biodurability—the ability of a material to maintain its physical and chemical integrity after implantation into living tissue—are essential for permanent medical implants. Materials chosen should avoid cytotoxicity, systemic toxicity, irritation, macroscopic or allergic reactions, muscle degeneration, or other adverse response. The biocompatibility and biodurability requirements significantly limit the selection of materials available for weight bearing devices.

The implant components must also exhibit sufficient strength and excellent fatigue performance to avoid mechanical failure over a long life under physiological loadings and kinematics. Properties such as yield strength, break strength, flexural strength, shear strength, and compressive strength of the implant components can significantly impact the success of the implant in weight bearing joint arthroplasty. Hard and stiff materials, such as ceramics or metals, have favorable strength characteristics. However, such materials have substantially higher flexural modules than that of cortical bone. This can cause a phenomenon known as "stress shielding," which may cause bone loss and the loosening and eventual failure of the implants. Certain polymer materials, having a flexural modulus similar to cortical bone, are thought to minimize stress shielding and the associated adverse effects. However, many polymers do not have sufficient yield strength to be used in weight bearing joints.

As exemplified in the devices described above, known hip, knee and ankle arthroplasty devices, and the majority of disc arthroplasty devices, incorporate articulation in their design. The articulation can be conforming, such as the ball and socket arrangement of the hip joint, or non-conforming, which permits sliding motion such as in known knee arthroplasty designs. In both conforming and non-conforming designs, the motion of the articulation surfaces against each other generates wear particulate. The primary wear that occurs in a hip prosthesis is between the femoral head and the acetabular cup. In a knee prosthesis, wear occurs primarily between the distal femoral condyles and the articulation surface of the tibial tray. The generation of wear particulate is important not only from a device lifetime perspective, but also from a biological perspective. In some cases, the biological response will dictate the lifetime of the device. This is because the generation of wear particulate in sufficient amount and size may lead to an adverse cellular response, manifested by macrophage activation, giant cell formation and a cascade of cytokine release ultimately leading to an imbalance in osteoclast and osteoblast activity. This may lead to inflammation of the tissue around the reconstructed joint, osteolysis and failure of the implant.

The use of ultra-high molecular weight polyethylene (UHMWPE) against metal in total joint replacements has a long clinical history dating back decades. UHMWPE was proposed as a counterface to stainless steel due to its greater biocompatibility and increased wear resistance over PTFE when evaluated on pin-on-plate wear testing simulators. UHMWPE also possesses superior mechanical toughness and wear resistance over most other polymers. UHMWPE on metal hip joints have succeeded clinically, with high rates of survivorship beyond 25 years in some cases. However, UHMWPE is also known to have certain drawbacks and limitations. These include the need for small diameter head sizes to reduce the frictional torque due to less than optimal lubrication, oxidation of the UHMWPE resulting from ionizing sterilization, and wear caused by third body debris such a bone particulate.

One disadvantage of UHMWPE is the accumulation of wear debris eliciting an adverse cellular response leading to inflammation and osteolysis of the surrounding bone. The literature suggests a threshold wear rate of 80 $mm^3$/year, above which particle induced osteolysis may lead to failure. The clinical wear rate of UHMWPE hip implants can potentially exceed this value. It has been suggested that the UHMWPE wear volume can be controlled below the indicated threshold for osteolysis by limiting the diameter of the femoral head. However, a smaller head decreases the range of motion of the joint and elevates the risk of the neck of the femoral stem impinging upon the cup causing dislocation of the femoral head.

The performance of UHMWPE on metal joint implants may also be adversely impacted by third-body wear particulate. For example, cements such as Polymethylmethacrylate (PMMA) are commonly used to secure the metal femoral stem of a hip prostheses into the femoral canal or the metal backing of the tibial tray to the tibial canal. PMMA particles can become entrapped between the head and UHMWPE acetabular cup. Such third-body wear particulate can also comprise bone or metal particles. This may lead to accelerated wear of the UHMWPE in such bearing couplings, either as a result of the abrasive effect of the particulate on the UHMWPE surface and/or by roughening the surface of the metal head bearing surface.

Ceramic on ceramic bearings have been found to have the lowest in vivo and in vitro wear rates to date of any bearing combination. Ceramic bearings do not share the same biological concerns from generated particulate debris as metal bearings, as they are considered to be relatively biologically inert. However, ceramics are prone to material failure when subjected to high mechanical stress, either in tensile or impact loading, which may limit their long term potential total weight bearing joint arthroplasty.

Other weight bearing joint replacement devices have been proposed that utilize compliant bearing surfaces provided as coatings of metal structural components. For example, one known attempt involved the use of a compliant material as a surface covering of a metal femoral ball articulating against the native cartilage of the acetabulum. Materials for use have included silicon rubbers, polyurethanes and olefin based synthetic rubbers. These devices have been shown to operate with very low friction because of the fluid-film lubrication that they exhibit, and therefore should produce lower wear than current prosthetic materials as the two surfaces of the joint are completely separated by a film of synovial fluid. They have been shown to possess a balance of physical strength, flexibility, dynamic flexural endurance, inherent chemical stability and physiological compatibility. The use of elastomers such as polyurethane as an articulating weight bearing material have not shown any benefit in terms of wear resistance over the more traditional bearing couples, and this may lead to questions regarding their biodurability and subsequent biocompatibility.

Thus, there is a need for weight bearing total joint arthroplasty devices having excellent strength, biocompatibility, biodurability, friction and wear characteristics for high performance, longer life and lower risk of adverse responses such as particulate induced inflammation and osteolysis. There is also need for such devices having articulating surfaces that do not produce potentially harmful metallic wear particulate. Ideally, known problems of using polymeric articulation surfaces, such as higher failure rates and the increased wear associated with strain hardening caused by multidirectional motion, could also be overcome. Such devices are needed for applications requiring conforming bearing surface, such as an acetabular cup for a hip joint, and also for high stress, non-conforming contact applications such as in a knee joint.

There is also an unmet need for devices that meet these requirements while also being substantially radiolucent for improved imaging of the affected area. Ideally, such devices would also have a modulus of elasticity closer to the adjacent bone tissue to minimize the adverse effects of stress shielding on the adjacent bone. There is a further need to reduce the number of components in such total joint arthroplasty devices so as to provide fewer modes of failure, to reduce parts inventory and simplify manufacturing and assembly. Such devices should also be readily sterilized using conventional radiation or steam sterilization techniques without causing oxidation and associated adverse effects. Ideally such devices could be provided for the major weight bearing joints in a range of sizes required to serve the full patient populations for various degenerative joint conditions.

BRIEF SUMMARY OF THE INVENTION

The present invention surprisingly provides compositions of unique crosslinking agents that include at least 2 (or more) photoactivatable groups; in particular diaryl ketone containing crosslinking agents, in combination with one or more polymerizable monomers. After application of the composition (with the crosslinking agent(s) and polymerizable monomer(s)), the composition is subjected to photochemical and/or thermal reaction conditions to form the brush polymer on a substrate surface.

Alternatively, the composition comprises a diaryl ketone, such as benzophenone and a polymerizable monomer, such as a zwitterionic monomer.

It should be understood, that throughout the present application, reference to the compositions of the invention refers to both mixtures; that is, a composition having a crosslinking agent that includes at least 2 (or more) photoactivatable groups, such as a diaryl ketone, in combination with one or more polymerizable monomers as well as a diaryl ketone, such as benzophenone, and a polymerizable monomer, such as a zwitterionic monomer.

The application of the composition for the treatment process can be sequential or simultaneous with regard to the addition of the components. That is, in one aspect, the crosslinking agent (or diaryl ketone) can be deposited onto the substrate and partially activated to cause the crosslinking agent to adhere to the surface. The polymerizable monomer can then be deposited to the substrate surface and then subjected to activation, thus resulting in the brush type polymeric layer. Alternatively, both the crosslinking agent (or diaryl ketone) and the monomer can be applied to the substrate surface at the same time and subjected to activation to form the brush type polymeric layer.

The inclusion of photoreactive moieties within the compositions provides that the composition can be used with a wide range of support surfaces. The compositions can be used alone or in combination with other materials to provide a desired surface characteristic. The compositions, alone or in combination with another material, provides the treated surface having a modified property that can include lubricity, hemocompatibility, wettability, hydrophilicity, biocompatibility and/or (decrease) bacterial adhesion.

In another aspect, the present invention pertains to lubricious compositions that are described herein. Such coatings can be used to coat medical devices, such as artificial joint components.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

DETAILED DESCRIPTION

Figure 1:
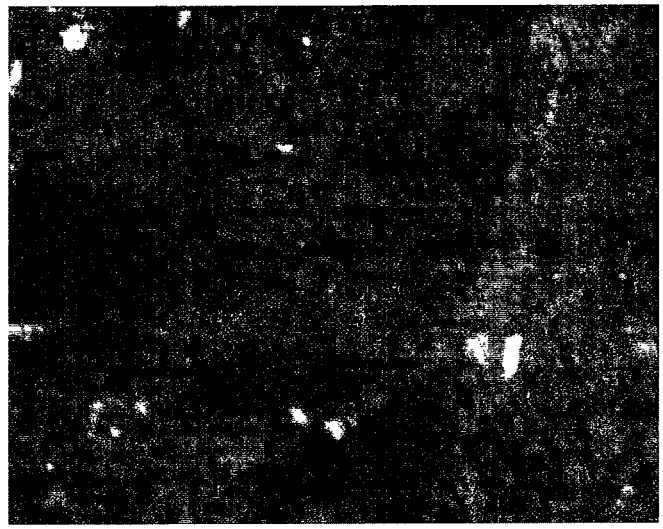
FIG. 1 demonstrates that nylon coupons treated with compositions of the invention have brush type polymer coatings.
Figure 1:
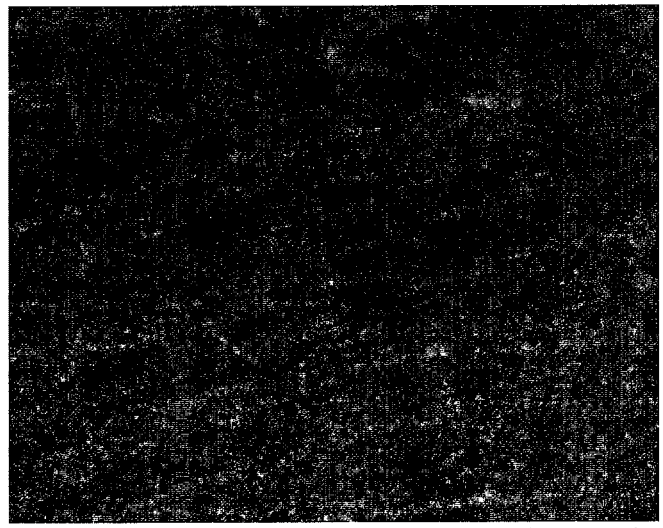
Figure 1:
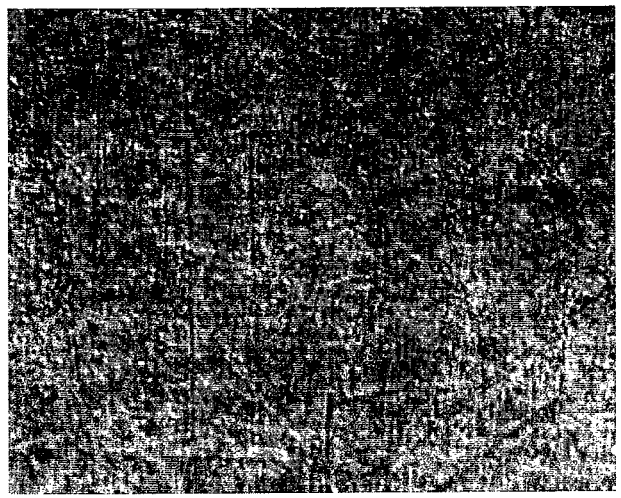

The present invention surprisingly provides compositions of unique crosslinking agents that include at least 2 (or more) photoactivatable groups; in particular diaryl ketone containing crosslinking agents, in combination with one or more polymerizable monomers.

Alternatively, as described above, the crosslinking agent can be substituted with a diaryl ketone. Both possibilities are represented throughout the application and are referred to as the "composition of the invention". In one aspect, zwitterionic polymerizable monomers are utilized in the coating.

In one aspect, the coatings produced by the compositions of the invention are hydrophilic in nature and do not promote non-specific binding interactions with non-target molecules.

In the specification and in the claims, the terms "including" and "comprising" are open-ended terms and should be interpreted to mean "including, but not limited to . . . ." These terms encompass the more restrictive terms "consisting essentially of" and "consisting of."

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

Crosslinking Agents:

The crosslinking agent (crosslinker) includes two or more pendent photoactive groups, described in detail herein, that are free radical generators, nitrene or carbene generators or combinations thereof, and include aryl ketones, azide/nitrene generators, chlorogenerating moieties (a free radical generator), carbene generators or diazo moieties.

The crosslinker can take on various forms, such as those described herein. The crosslinker includes at least two (2) pendent photoactive groups. A general formula for photoactivatable crosslinkers comprises:

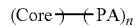

(Core)—(PA)$_n$ wherein "core" is a linear or branched alkyl group, a linear or branched alkenyl group, an aryl group, a sugar substrate, a polysaccharide substrate, a peptide, a protein, a nucleic acid, an oligonucleotide, polyacrylics, polyvinyls, nylons, polyurethanes, or polyethers.

Each "PA", independently, is a photoactivatable group that can be an aryl ketone, an azide or nitrene generator, a free radical generator, a carbene generator or a diazo moiety.

"n" is an integer from at least 2 to about 5,000, for example from at least 2 to about 1,000, from at least 2 to about 500, from at least 2 to about 100, including all integers and ranges from at least 2 and 5,000, e.g., from about 3 to about 5,000, from about 4 to about 5,000, from at least 2 to about 4,999, etc.

Additionally, suitable photoactivatable crosslinkers include those described in U.S. Pat. Nos. 5,414,075; 5,637,460; 5,714,360; 6,077,698 and 6,278,018, the contents of which are incorporated herein in their entirety for all purposes and most particularly column 5, line 1 through line 15 and column 8, line 5 through line 30 of U.S. Pat. No. 5,414,075; column 5, line 1 through line 24 and column 8, line 1 through line 20 of U.S. Pat. No. 5,637,460; column 5 through column 8 and column 9, line 1 through line 40 of U.S. Pat. No. 5,714,360; column 7 through column 8 and column 9, line 1 through line 40 of U.S. Pat. No. 6,077,698; column 3 through column 4 and column 5, line 1 through line 28 of U.S. Pat. No. 6,278,018; and column 5, line 1 through line 15 and column 8, line 5 through line 30 of U.S. Pat. No. 5,414,075.

In one aspect, use of photoreactive (photoactive) species as pendent groups within the crosslinkers described herein are generally in the form of photoreactive aryl ketones moieties, such as acetophenone, benzophenone, anthraquinone, anthrone, and anthrone-like heterocycles (i.e., heterocyclic analogs of anthrone such as those having N, O, or S in the 10-position), or their substituted (e.g., ring substituted) derivatives. Examples of aryl ketones include heterocyclic derivatives of anthrone, including acridone, xanthone, and thioxanthone, and their ring substituted derivatives. In particular, thioxanthone, and its derivatives, having excitation wavelengths greater than about 360 nm are useful.

The functional groups of ketones are preferred since they are readily capable of undergoing an activation/inactivation/reactivation cycle. Benzophenone is a photoreactive moiety, since it is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (e.g., carbon-hydrogen) is not available for bonding, the ultraviolet light-induced excitation of the benzophenone group is reversible and the molecule returns to ground state energy level upon removal of the energy source. Photoactivatable aryl ketones such as benzophenone and acetophenone are of particular importance inasmuch as these groups are subject to multiple reactivation in water and hence provide increased coating efficiency.

It should be understood that with reference to a photoreactive moiety, the pendent photoreactive groups include free radical generators, nitrene and carbene generators or combinations thereof, as being part of the crosslinker, that the photoreactive moiety is attached to the remainder of the crosslinker via a bond or a linking group that joins the photoreactive moiety to the remainder of the molecule. In other words, for example, there are benzophenone fragments that are included in the crosslinker, such that the ketone functionality remains.

Suitable crosslinking agents, described herein, can include one or more hydrophilic portions, i.e., a hydroxyl group (that may be protected), amines, alkoxy groups, etc.

In one embodiment the crosslinking agent has the formula:

L-((D-T-C(R$^1$)(XP)CHR$^2$GR$^3$C(=O)R$^4$))$_m$.

L is a linking group. D is O, S, SO, SO$_2$, NR$^5$ or CR$^6$R$^7$. T is (—CH$_2$—)$_x$, (—CH$_2$CH$_2$—O—)$_x$, (—CH$_2$CH$_2$CH$_2$—O—)$_x$, (—CH$_2$CH$_2$CH$_2$CH$_2$—O—)$_x$ or forms a bond. R$^1$ is a hydrogen atom, an alkyl, alkyloxyalkyl, aryl, aryloxyalkyl or aryloxyaryl group. X is O, S, or NR$^8$R$^9$. P is a hydrogen atom or a protecting group, with the proviso that P is absent when X is $NR^8R^9$. $R^2$ is a hydrogen atom, an alkyl, alkyloxyalkyl, aryl, aryloxylalkyl or aryloxyaryl group. G is O, S, SO, $SO_2$, $NR^{10}$, $(CH_2)_r$—O— or C=O. $R^3$ and $R^4$ are each independently an alkyl, aryl, arylalkyl, heteroaryl, or a heteroarylalkyl group, or optionally, $R^3$ and $R^4$ can be tethered together via (—$CH_2$—)$_q$, (—$CH_2$—)$_r$C=O(—$CH_2$—)$_s$, (—$CH_2$—)$_r$S(—$CH_2$—)$_s$, (—$CH_2$—)$_r$S=O(—$CH_2$—)$_s$, (—$CH_2$—)$_r$S(O)$_2$(—$CH_2$—)$_s$, or (—$CH_2$—)$_r$NR(—$CH_2$—)$_s$. $R^5$ and $R^{10}$ are each independently a hydrogen atom or an alkyl, aryl, or arylalkyl group. $R^6$ and $R^7$ are each independently a hydrogen atom, an alkyl, aryl, arylalkyl, heteroaryl or heteroarylalkyl group. $R^8$ and $R^9$ are each independently a hydrogen atom, an alkyl, aryl, or arylalkyl group, R is a hydrogen atom, an alkyl group or an aryl group, q is an integer from 1 to about 7, r is an integer from 0 to about 3, s is an integer from 0 to about 3, m is an integer from 2 to about 10, t is an integer from 1 to about 10 and x is an integer from 1 to about 500.

In one aspect, L is a branched or unbranched alkyl chain having between about 2 and about 10 carbon atoms.

In another aspect, D is an oxygen atom (O).

In still another aspect, T is (—$CH_2$—)$_x$ or (—$CH_2CH_2$—O—)$_x$ and x is 1 or 2.

In still yet another aspect, $R^1$ is a hydrogen atom.

In yet another aspect, X is an oxygen atom, O, and P is a hydrogen atom.

In another aspect, $R^2$ is a hydrogen atom.

In still another aspect, G is an oxygen atom, O.

In still yet another aspect, $R^3$ and $R^4$ are each individually aryl groups, which can be further substituted, and m is 3.

In one particular aspect, L is

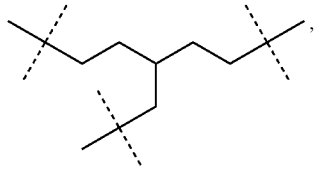

D is O, T is (—$CH_2$—)$_x$, $R^1$ is a hydrogen atom, X is O, P is a hydrogen atom, $R^2$ is a hydrogen atom, G is O, $R^3$ and $R^4$ are phenyl groups, m is 3 and x is 1.

In yet another particular aspect, L is (—$CH_2$—)$_y$, D is O, T is (—$CH_2$—)$_x$, $R^1$ is a hydrogen atom, X is O, P is a hydrogen atom, $R^2$ is a hydrogen atom, G is O, $R^3$ and $R^4$ are phenyl groups, m is 2, x is 1 and y is an integer from 2 to about 6, and in particular, y is 2, 4 or 6.

In certain embodiments, x is an integer from about 1 to about 500, more particularly from about 1 to about 400, from about 1 to about 250, from about 1 to about 200, from about 1 to about 150, from about 1 to about 100, from about 1 to about 50, from about 1 to about 25 or from about 1 to about 10

In another embodiment, the family has the formula:

wherein L, T, $R^1$, X, P, $R^2$, G, $R^3$, $R^4$, $R^8$, $R^9$, $R^{10}$, R, q, r, s, m, t and x are as defined above.

In one aspect, L has a formula according to structure (I):

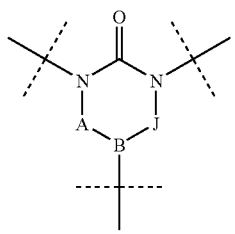

(I)

A and J are each independently a hydrogen atom, an alkyl group, an aryl group, or together with B form a cyclic ring, provided when A and J are each independently a hydrogen atom, an alkyl group, or an aryl group then B is not present, B is $NR^{11}$, O, or (—$CH_2$—)$_z$, provided when A, B and J form a ring, then A and J are (—$CH_2$—)$_z$ or C=O, $R^{11}$ is a hydrogen atom, an alkyl group, an aryl group or denotes a bond with T, each z independently is an integer from 0 to 3 and provided when either A or J is C=O, then B is $NR^{11}$, O, or (—$CH_2$—)$_z$ and z must be at least 1.

In another aspect T is —$CH_2$—.

In another embodiment, the family has the formula:

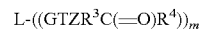

L-((GTZR$^3$C(=O)R$^4$))$_m$ wherein L, T, G, $R^3$, $R^4$, $R^{10}$, R, q, r, s, m, t and x are as defined above. Z can be a C=O, COO or CONH when T is (—$CH_2$—)$_x$.

In one aspect, L has a formula according to structure (I):

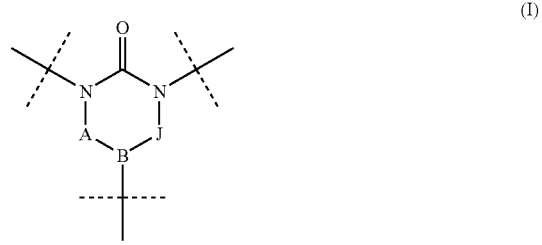

(I)

wherein A, B, J, $R^{11}$, and z are as defined above.

In another aspect, L has a formula according to structure (II):

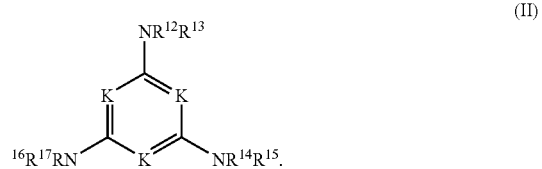

(II)

$R^{12}$, $R^{13}$, $R^{14}$, $R^{15}$, $R^{16}$, $R^{17}$ are each independently a hydrogen atom, an alkyl or aryl group or denotes a bond with T, provided at least two of $R^{12}$, $R^{13}$, $R^{14}$, $R^{15}$, $R^{16}$, $R^{17}$ are bonded with T and each K, independently is CH or N.

In another embodiment, the crosslinking agent has the formula:

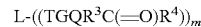

L-((TGQR$^3$C(=O)R$^4$))$_m$ wherein L, G, $R^3$, $R^4$, $R^{10}$, R, q, r, s, m, t and x are as defined above. T is (—$CH_2$—)$_x$, (—$CH_2CH_2$—O—)$_x$, (—$CH_2CH_2CH_2$—O—)$_x$, (—$CH_2CH_2CH_2CH_2$—O—)$_x$ or forms a bond. Q is (—$CH_2$—)$_p$, (—$CH_2CH_2$—O—)$_p$, (—$CH_2CH_2CH_2$—O—)$_p$ or (—$CH_2CH_2CH_2CH_2$—O—)$_p$ and p is an integer from 1 to about 10.

In one aspect, L has a formula according to structure (I):

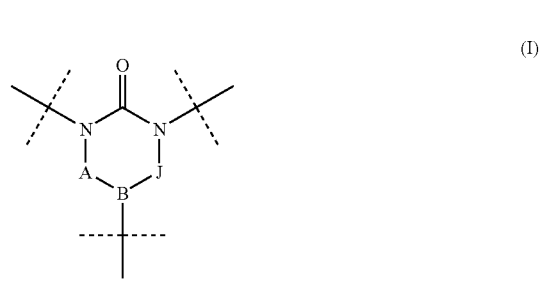

(I)

wherein A, B, J, $R^{11}$, and z are as defined above.

In another aspect, L has a formula according to structure (II):

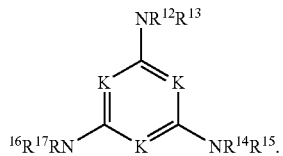

(II)

$R^{12}$, $R^{13}$, $R^{14}$, $R^{15}$, $R^{16}$, $R^{17}$ are each independently a hydrogen atom, an alkyl or aryl group or denotes a bond with T, provided at least two of $R^{12}$, $R^{13}$, $R^{14}$, $R^{15}$, $R^{16}$, $R^{17}$ are bonded with T and each K, independently is CH or N.

In still yet another aspect, compounds of the present invention provide that $R^3$ and $R^4$ are both phenyl groups and are tethered together via a CO, a S or a $CH_2$.

In yet another aspect, compounds of the present invention provide when $R^3$ and $R^4$ are phenyl groups, the phenyl groups can each independently be substituted with at least one alkyloxyalkyl group, such as $CH_3O$—$(CH_2CH_2O$—$)_n$—, or $CH_3O($—$CH_2CH_2CH_2O$—$)_n$- a hydroxylated alkoxy group, such as HO—$CH_2CH_2O$—, HO($—CH_2CH_2O$—$)_n$— or HO($—CH_2CH_2CH_2O$—$)_n$—, etc. wherein n is an integer from 1 to about 10.

In another embodiment the crosslinking agent has the formula:

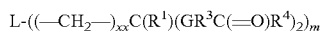

wherein L, each R, $R^1$, each G, each $R^3$, each $R^4$, each $R^{10}$, each q, each r, each s, each t and m are as defined above and xx is an integer from 1 to about 10.

In one aspect, L has a formula according to structure (I):

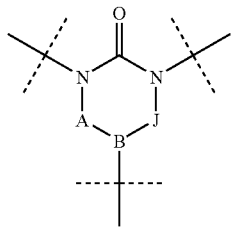

(I)

wherein A, B, J, $R^{11}$, and z are as defined above.

In another aspect, A and B are both hydrogen atoms.

In still another aspect, xx is 1.

In yet another aspect, $R^1$ is H.

In still yet another aspect, G is (—$CH_2$—$)_tO$— and t is 1.

In another aspect, $R^3$ and $R^4$ are each individually aryl groups.

In still yet another embodiment, xx is 1, $R^1$ is H, each G is (—$CH_2$—$)_tO$—, t is 1 and each of $R^3$ and $R^4$ are each individually aryl groups.

In another embodiment of the invention, the family has the formula

where L, R, $R^1$, $R^2$, $R^3$, $R^4$, $R^8$, $R^9$, $R^{10}$, X, P, G, q, r, s, t, and m are as defined above.

In one aspect, L is

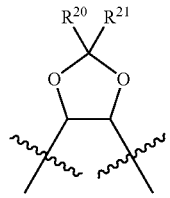

and $R^{20}$ and $R^{21}$ are each individually a hydrogen atom, an alkyl group or an aryl group.

In another aspect, $R^1$ is H.

In still another aspect, wherein X is O.

In yet another aspect, P is H.

In still yet another aspect, $R^2$ is H.

In another aspect, G is (—$CH_2$—$)tO$— and t is 1.

In still another aspect, $R^3$ and $R^4$ are each individually aryl groups.

In yet another aspect, $R^1$ is H, X is O, P is H, $R^2$ is H, G is (—$CH_2$—$)_tO$—, t is 1, $R^3$ and $R^4$ are each individually aryl groups and $R^{20}$ and $R^{21}$ are both methyl groups.

In yet another embodiment, the present invention provides crosslinking agents having the formula:

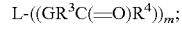

where L, G, R, $R^3$, $R^4$, $R^{10}$, q, r, s, m and t are as defined above.

In one aspect, L is

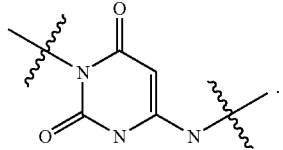 [SMILES: *Nc1cc(=O)n(*)c(=O)[nH]1]

In another aspect, G is C=O.

In still another aspect, $R^3$ and $R^4$ are each individually aryl groups.

In yet another aspect, G is C=O and $R^3$ and $R^4$ are each individually aryl groups.

Such crosslinking agents are described in U.S. Ser. No. 11/423,503 (US Publication No. 20070003707), the contents of which are incorporated herein by reference.

Crosslinking agents encompassed by the present invention can be prepared by selection of an appropriate aryl group with a photoactivatable group and at least one group that can either act as a nucleophilic site or can be acted upon in a nucleophilic displacement reaction with a linking agent (L) having at least two opposing groups, either a leaving group(s) or a nucleophilic group(s). General synthetic schemes detailed below demonstrate two approaches suitable to prepare compounds of the invention.

Scheme I

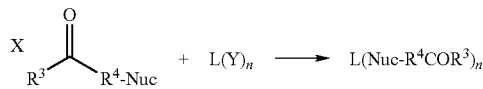

or

Scheme II

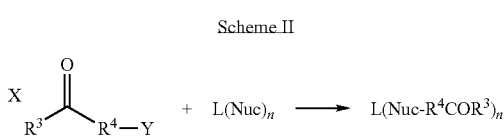

wherein X is an integer equivalent to "n" and n is an integer between 2 and about 6, $R^3$ and $R^4$ are as defined above, "Y" is a leaving group or a group that can be acted upon by a nucleophilic group, such as an ester, carboxylic acid halide, etc. and "Nuc" is a nucleophilic group, as described in further detail below. Alternatively, the reaction between "Y" and "Nuc" can be a condensation reaction, such as the reaction between, for example, a hydroxyl group and a carboxylic acid.

It should be understood in schemes I and II, that $R^3$ and $R^4$ are interchangeable.

Suitable nucleophilic groups (Nuc) include, for example, amines, hydroxyl, thiol, etc.

Suitable leaving groups, or groups susceptible to nucleophilic attack, include esters, ethers, epoxides, halides, isocyanates, isothiocyanates, sulfonyl chlorides, anhydrides, carboxylic acid halides, carboxylic acid esters, and aldehydes.

Resultant functional moieties from the reaction between the nucleophilic group and leaving (or condensation group) include, for example, esters, ethers, carbamates, thiocarbamates, sulfones, amides, ureas, thiourea, amines, sulfonamides, imines (that can be further reduced with a reducing agent such as sodium borohydride to an amine), etc.

Suitable reaction conditions for such condensations or nucleophilic displacements are known in the art. For example, hydroxyl containing moieties can be condensed with a carboxylic acid under dehydrating conditions (refluxing toluene, acid catalyst, Dean Stark trap) to form esters. Reactive halides can be displaced by hydroxyl groups under basic conditions. An isocyanate reacts with a hydroxyl group with heat to form carbamates. Likewise, an isothiocyanates reacts with a hydroxyl group to form a thiocarbamate. Under deprotonation conditions, a hydroxide ion reacts with an epoxide to form an ether linkage and forming a new hydroxyl group. Reaction between a hydroxyl and a sulfonyl chloride forms a sulfone. Reaction between a hydroxyl and an anhydride will form a ester with a carboxylic acid portion as well. Reaction between a hydroxyl group and an ester will also form an ester, with the removal of a corresponding displaced alcohol, generally under conditions that drive off the displaced alcohol.

Much like the reactions with hydroxyl groups, amines serve in similar manner. For example, an amine can react with an activated carboxylic acid for form an amide. Activation of a carboxylic acid can be facilitated by various methods in the art, including for example, use of dicyclohexylcarbodiimide (DCC) that generates urea as a side product. An isocyanate reacts with an amine to form a urea and an isothiocyanate reacts with an amine to form a thiourea.

Reaction between an amine and an epoxide will form an amine with an appended hydroxyl group from the nucleophilic displacement of the epoxide ring. Reaction between an amine and a sulfonyl chloride will form a sulfonamide. Reaction between an anhydride and an amine will afford an amide with a carboxylic portion attached to the product. Reaction between an aldehyde and an amine will form an imine which can be further reduced to an amine. Reaction between a carboxylic acid halide and an amine will form an amide, as well as the reaction between a carboxylic ester and amine. Lastly, melamine type compounds can react with an amine to form amine linkages.

Reaction conditions to form the compounds of the invention are known in the art. For example, suitable reaction conditions are described in "March's Advanced Organic Chemistry: Reactions, Mechanisms, and Structure, 5th Edition, John Wiley & Sons, Michael B. Smith & Jerry March; Fieser and Fieser's Reagents for Organic Synthesis" John Wiley & Sons, NY; Vogel's Textbook of Practical Organic Chemistry (Fifth Edition) by A. I. Vogel, B. S. Furniss, A. J. Hannaford, P. W. G. Smith, and A. R. Tatchell, Longman Scientific and Technical, Longman Group UK; and Advanced Organic Chemistry parts A and B" Third Edition, F. A. Carey, R. S. Sundberg, Plenum Press, NY, 1990, the contents of which are incorporated herein by reference in their entirety.

It should also be understood that each "Y" independently can be different. Therefore, it is possible to have reaction products that include an ether linkage as well as an ester linkage to the carbonyl containing photoactivatable group.

An exemplary non-limiting reaction is depicted in Scheme III, in which a hydroxyl group undergoes nucleophilic addition to an ester or acid halide or can undergo a condensation reaction between the hydroxyl group and a carboxylic acid.

Scheme III

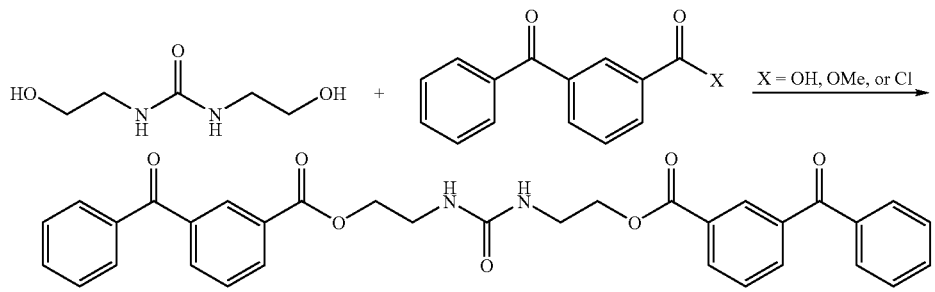

Polymerizable Monomers:

"Polymerizable monomer" means a polymerizable allylic, vinylic, methacrylic or acrylic compound. The monomer can be anionic, cationic, zwitterionic, or nonionic.

Examples of monofunctional polymerizable monomers include styrene, methyl(meth)acrylate, ethyl(meth)acrylate, butyl(meth)acrylate, 2-ethylhexyl(meth)acrylate, lauryl (meth)acrylate, cyclohexyl(meth)acrylate, cyclohexenyl (meth)acrylate, 2-hydroxyl(meth)acrylate, hydroxypropyl (meth)acrylate, tetrahydrofurfuryl(meth)acryl ate, 6-caprolactone-modified tetrahydrofurfuryl(meth)acrylate, phenoxyethyl(meth)acrylate, phenoxy polyethylene glycol (meth)acrylate, dicyclopentenyl(meth)acrylate, dicyclopentenyloxyethyl(meth)acrylate, isobornyl(meth)acrylate, benzyl(meth)acrylate, 6-caprolactone-modified hydroxyethyl (meth)acrylate, polyethylene glycol mono(meth)acrylate, polypropylene glycol mono(meth)acrylate, 2-hydroxy-3-phenoxypropyl(meth)acrylate, 2-hydroxy-3-butoxypropyl (meth)acrylate, phthalic acid monohydroxyethyl(meth)acrylate, para-cumylphenol ethylene oxide-modified (meth) acrylate, N-methylol(meth)acrylamide, N-methylol(meth) acrylamide butyl ether, acryloyl morpholine, dimethylaminoethyl(meth)acrylate, N-vinyl-2-pyrrolidone, etc.

In addition to the poly(meth)acryl compound monomers, oligomers, and polymers previously mentioned, useful free-radically polymerizable monomers include, for example, styrene and substituted styrenes (e.g., 1,4-divinylbenzene, alpha-methylstyrene); vinyl esters (e.g., vinyl acetate); vinyl ethers (e.g., butyl vinyl ether); N-vinyl compounds (e.g., N-vinyl-2-pyrrolidone, N-vinylcaprolactam); acrylamide and substituted acrylamides (e.g., N,N-dialkylacrylamide); monofunctional(meth)acrylates (e.g., isooctyl(meth)acrylate, nonylphenol ethoxylate(meth)acrylate, isononyl(meth) acrylate, diethylene glycol(meth)acrylate, isobornyl(meth) acrylate, 2-(2-ethoxyethoxy)ethyl(meth)acrylate, 2-ethylhexyl(meth)acrylate, lauryl(meth)acrylate, butanediol mono(meth)acrylate, beta-carboxyethyl(meth)acryl ate, isobutyl(meth)acrylate, 2-hydroxyethyl(meth)acrylate, (meth)acrylonitrile, maleic anhydride, itaconic acid, isodecyl (meth)acrylate, dodecyl(meth)acrylate, n-butyl(meth)acrylate, methyl(meth)acrylate, hexyl(meth)acrylate, (meth) acrylic acid, stearyl(meth)acrylate, hydroxy functional polycaprolactone ester(meth)acrylate, hydroxypropyl(meth) acrylate, hydroxyisopropyl(meth)acrylate, hydroxybutyl (meth)acrylate, tetrahydrofurfuryl(meth)acrylate, cyclohexyl(meth)acrylate, n-hexyl(meth)acrylate, 2-ethoxyethyl (meth)acrylate, isodecyl(meth)acrylate, 2-methoxyethyl (meth)acrylate, 2-(2-ethoxyethoxy)ethyl(meth)acrylate, lauryl(meth)acrylate, 2-phenoxyethyl(meth)acrylate, isocyanatoethyl(meth)acrylate, glycidyl(meth)acrylate, benzyl (meth)acrylate, tridecyl(meth)acrylate, caprolactone(meth) acrylate, hydroxyisobutyl(meth)acrylate, and tetrahydrofurfuryl(meth)acrylate); and combinations thereof Such compounds are widely available from vendors such as, for example, Sartomer Company, Exton, Pa.; UCB Chemicals Corporation, Smyrna, Ga.; and Aldrich Chemical Company, Milwaukee, Wis.

"Cationic monomer" means a monomer which possesses a net positive charge. Representative cationic monomers include the quaternary or acid salts of dialkylaminoalkyl acrylates and methacrylates, the quaternary or acid salts of dialkylaminoalkylacrylamides and methacrylamides, N,N-diallyldialkyl ammonium halides, Mannich products, and the like. Alkyl groups are generally C1-C4 alkyl. Cationic monomers include diallyldimethylammonium chloride (DADMAC), (3-acrylamidopropyl)trimethylammonium chloride (APTAC), (3-methacrylamido)propyltrimethylammonium chloride (MAPTAC), dimethylaminoethylacrylate methyl chloride quaternary salt (DMAEA/MCQ), dimethylaminoethylmethacrylate methyl chloride quaternary salt (DMAEM/MCQ) and dimethylaminoethylacrylate benzyl chloride quaternary salt (DMAEA/BCQ).

"Anionic monomer" means a monomer which possesses a net negative charge. Representative anionic monomers include metal salts of acrylic acid, methacrylic acid, or itaconic acid, 2-acrylamido-2-methyl propane sulfonate, sulfopropyl acrylate or methacrylate or other water-soluble forms of these or other polymerizable carboxylic or sulphonic acids, sulphomethylated acrylamide, allyl sulphonate, sodium vinyl sulphonate, monoacryloxyethyl phosphate and their sodium salts and the like.

"Nonionic monomer" means a monomer which is electrically neutral (contains no ionized groups). Representative nonionic monomers include acrylamide, methacrylamide, N-methylacrylamide, N,N-dimethyl(meth)acrylamide, N-isopropyl(meth)acrylamide, N-(2-hydroxypropyl)methacrylamide, N-methylolacrylamide, N-vinylformamide, N-vinylacetamide, N-vinyl-N-methylacetamide, poly(ethylene glycol)(meth)acrylate, poly(ethylene glycol) monomethyl ether mono(meth)acrylate, N-vinyl-2-pyrrolidone, glycerol mono((meth)acrylate), 2-hydroxyethyl(meth)acrylate, vinyl methylsulfone, vinyl acetate, and the like.

"Zwitterionic monomer" means a polymerizable molecule containing cationic and anionic (charged) functionality in equal proportions, so that the molecule is net neutral overall. Representative Zwitterionic monomers include N,N-dimethyl-N-acryloyloxyethyl-N-(3-sulfopropyl)-ammonium betaine, N,N-dimethyl-N-methacryloyloxyethyl-N-(3-sulfopropyl)-ammonium betaine, N,N-dimethyl-N-acrylamidopropyl-N-(2-carboxymethyl)-ammonium betaine, N,N-dimethyl-N-methacrylamidopropyl-N-(2-carboxymethyl)-ammonium betaine, N,N-dimethyl-N-acrylamidopropyl-N-(3-sulfopropyl)-ammonium betaine, N,N-dimethyl-N-methacrylamidopropyl-N-(3-sulfopropyl)-ammonium betaine (SBMAM), N,N-dimethyl-N-acrylamidopropyl-N-(2-carboxymethyl)-ammonium betaine, N,N-dimethyl-N-methacrylamidopropyl-N-(2-carboxymethyl)-ammonium betaine, 2-(methylthio)ethyl methacryloyl-S-(sulfopropyl)-sulfonium betaine, 2-[(2-acryloylethyDdimethylammonio] ethyl 2-methyl phosphate, 2-(acryloyloxyethyl)-2'-(trimethylammonium)ethyl phosphate, [(2-acryloylethyl) dimethylammonio]methyl phosphonic acid, 2-[(3-acrylamidopropyl)dimethylammonio]ethyl 2'-isopropyl phosphate (AAPI), 1-vinyl-3-(3-sulfopropyl)imidazolium hydroxide, (2-acryloxyethyl)carboxymethyl methylsulfonium chloride, 1-(3-sulfopropyl)-2-vinylpyridinium betaine, N-(4-sulfobutyl)-N-methyl-N,N-diallylamine ammonium betaine (MDABS), or N,N-diallyl-N-methyl-N-(2-sulfoethyl) ammonium betaine, 2-methacryloyloxyethyl phosphorylcholine, and the like.

In one aspect, 2-methacryloyloxyethyl phosphorylcholine is not included as a monomer.

Diaryl Ketones:

Suitable aryl ketones useful in the compositions of the invention include, for example but are not limited to, acetophenone, benzophenone, anthraquinone, anthrone, and anthrone-like heterocycles (i.e., heterocyclic analogs of anthrone such as those having N, O, or S in the 10-position), or their substituted (e.g., ring substituted) derivatives. Examples of aryl ketones include heterocyclic derivatives of anthrone, including acridone, xanthone, and thioxanthone, and their ring substituted derivatives. In particular, thioxanthone, and its derivatives, having excitation wavelengths greater than about 360 nm are useful.

Terminology:

"Alkyl" by itself or as part of another substituent refers to a saturated or unsaturated branched, straight-chain or cyclic monovalent hydrocarbon radical having the stated number of carbon atoms (i.e., C1-C6 means one to six carbon atoms) that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. "Lower alkyl" refers to alkyl groups having from 1 to 6 carbon atoms.

"Alkanyl" by itself or as part of another substituent refers to a saturated branched, straight-chain or cyclic alkyl derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" by itself or as part of another substituent refers to an unsaturated branched, straight-chain or cyclic alkyl having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkyloxyalkyl" refers to a moiety having two alkyl groups tethered together via an oxygen bond. Suitable alkyloxyalkyl groups include polyoxyalkylenes, such as polyethyleneoxides, polypropyleneoxides, etc. that are terminated with an alkyl group, such as a methyl group. A general formula for such compounds can be depicted as R'—(OR")$_n$ or (R'O)$_n$—R" wherein n is an integer from 1 to about 10, and R' and R" are alkyl or alkylene groups.

"Alkynyl" by itself or as part of another substituent refers to an unsaturated branched, straight-chain or cyclic alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkyldiyl" by itself or as part of another substituent refers to a saturated or unsaturated, branched, straight-chain or cyclic divalent hydrocarbon group having the stated number of carbon atoms (i.e., C1-C6 means from one to six carbon atoms) derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-di yl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies be on the same carbon atom, the nomenclature "alkylidene" is used. A "lower alkyldiyl" is an alkyldiyl group having from 1 to 6 carbon atoms. In preferred embodiments the alkyldiyl groups are saturated acyclic alkanyldiyl groups in which the radical centers are at the terminal carbons, e.g., methandiyl (methano); ethan-1,2-diyl (ethano); propan-1,3-diyl (propano); butan-1, 4-diyl (butano); and the like (also referred to as alkylenes, defined infra).

"Alkylene" by itself or as part of another substituent refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkylene is indicated in square brackets. Typical alkylene groups include, but are not limited to, methylene (methano); ethylenes such as ethano, etheno, ethyno; propylenes such as propano, prop[1]eno, propa[1,2]dieno, prop[1]yno, etc.; butylenes such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In preferred embodiments, the alkylene group is (C1-C6) or (C1-C3) alkylene. Also preferred are straight-chain saturated alkano groups, e.g., methano, ethano, propano, butano, and the like.

"Aryl" by itself or as part of another substituent refers to a monovalent aromatic hydrocarbon group having the stated number of carbon atoms (i.e., C5-C15 means from 5 to 15 carbon atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like, as well as the various hydro isomers thereof. In preferred embodiments, the aryl group is (C5-C15) aryl, with (C5-C10) being even more preferred. Particularly preferred aryls are phenyl and naphthyl.

"Arylalkyl" by itself or as part of another substituent refers to an acyclic alkyl radical in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. Preferably, an arylalkyl group is $(C_7-C_{30})$ arylalkyl, e.g., the alkanyl, alkenyl or alkynyl moiety of the arylalkyl group is $(C_1-C_{10})$ and the aryl moiety is $(C_6-C_{20})$, more preferably, an arylalkyl group is $(C_7-C_{20})$ arylalkyl, e.g., the alkanyl, alkenyl or alkynyl moiety of the arylalkyl group is $(C_1-C_8)$ and the aryl moiety is $(C_6-C_{12})$.

"Aryloxyalkyl" refers to a moiety having an aryl group and an alkyl group tethered together via an oxygen bond. Suitable aryloxyalkyl groups include phenyloxyalkylenes, such as methoxyphenyl, ethoxyphenyl, etc.

"Cycloalkyl" by itself or as part of another substituent refers to a cyclic version of an "alkyl" group. Typical cycloalkyl groups include, but are not limited to, cyclopropyl; cyclobutyls such as cyclobutanyl and cyclobutenyl; cyclopentyls such as cyclopentanyl and cycloalkenyl; cyclohexyls such as cyclohexanyl and cyclohexenyl; and the like.

"Cycloheteroalkyl" by itself or as part of another substituent refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, imidazolidine, morpholine, piperazine, piperidine, pyrazolidine, pyrrolidine, quinuclidine, and the like.

"Halogen" or "Halo" by themselves or as part of another substituent, unless otherwise stated, refer to fluoro, chloro, bromo and iodo.

"Haloalkyl" by itself or as part of another substituent refers to an alkyl group in which one or more of the hydrogen atoms are replaced with a halogen. Thus, the term "haloalkyl" is meant to include monohaloalkyls, dihaloalkyls, trihaloalkyls, etc. up to perhaloalkyls. For example, the expression "(C1-C2) haloalkyl" includes fluoromethyl, difluoromethyl, trifluoromethyl, 1-fluoroethyl, 1,1-difluoroethyl, 1,2-difluoroethyl, 1,1,1-trifluoroethyl, perfluoroethyl, etc.

"Heteroalkyl, Heteroalkanyl, Heteroalkenyl, Heteroalkynyl" by itself or as part of another substituent refer to alkyl, alkanyl, alkenyl and alkynyl radical, respectively, in which one or more of the carbon atoms (and any associated hydrogen atoms) are each independently replaced with the same or different heteroatomic groups. Typical heteroatomic groups include, but are not limited to, —O—, —S—, —O—O—, —S—S—, —O—S—, —NR'—, =N—N=, —N=N—, —N=N—NR'—, —PH—, —P(O)$_2$—, —O—P(O)$_2$—, —S(O)—, —S(O)$_2$—, —SnH$_2$— and the like, where R' is hydrogen, alkyl, substituted alkyl, cycloalkyl, substituted cycloalkyl, aryl or substituted aryl.

"Heteroaryl" by itself or as part of another substituent, refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, β-carboline, benzoxazine, benzimidazole, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is from 5-20 membered heteroaryl, more preferably from 5-10 membered heteroaryl. Preferred heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent refers to an acyclic alkyl group in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylakenyl and/or heteroarylalkynyl is used. In preferred embodiments, the heteroarylalkyl group is a 6-21 membered heteroarylalkyl, e.g., the alkanyl, alkenyl or alkynyl moiety of the heteroarylalkyl is (C1-C6) alkyl and the heteroaryl moiety is a 5-15-membered heteroaryl. In particularly preferred embodiments, the heteroarylalkyl is a 6-13 membered heteroarylalkyl, e.g., the alkanyl, alkenyl or alkynyl moiety is (C1-C3) alkyl and the heteroaryl moiety is a 5-10 membered heteroaryl.

"Hydroxyalkyl" by itself or as part of another substituent refers to an alkyl group in which one or more of the hydrogen atoms are replaced with a hydroxyl substituent. Thus, the term "hydroxyalkyl" is meant to include monohydroxyalkyls, dihydroxyalkyls, trihydroxyalkyls, etc.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, tetrahydronaphthalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, tetrahydronaphthalene, triphenylene, trinaphthalene, and the like, as well as the various hydro isomers thereof.

"Parent Heteroaromatic Ring System" refers to a parent aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Leaving group" is a group that is displaced during a reaction by a nucleophilic reagent. Suitable leaving groups include S(O)$_2$Me, —SMe or halo (e.g., F, Cl, Br, I).

"Linking group" is a group that serves as an intermediate locus between two or more end groups. The nature of the linking group can vary widely, and can include virtually any combination of atoms or groups useful for spacing one molecular moiety from another. For example, the linker may be an acyclic hydrocarbon bridge (e.g, a saturated or unsaturated alkyleno such as methano, ethano, etheno, propano, prop[1]eno, butano, but[1]eno, but[2]eno, buta[1,3]dieno, and the like), a monocyclic or polycyclic hydrocarbon bridge (e.g., [1,2]benzeno, [2,3]naphthaleno, and the like), a simple acyclic heteroatomic or heteroalkyldiyl bridge (e.g., —O—, —S—, —S—O—, —NH—, —PH—, —C(O)—, —C(O)NH—, —S(O)—, —S(O)$_2$—, —S(O)NH—, —S(O)$_2$NH—, —O—CH$_2$—, —CH$_2$—O—CH$_2$—, —O—CH=CH—CH$_2$—, and the like), a monocyclic or polycyclic heteroaryl bridge (e.g., [3,4]furano, pyridino, thiopheno, piperidino, piperazino, pyrazidino, pyrrolidino, and the like) or combinations of such bridges.

"Polymer brush" refers to a polymeric chain that is formed from a polymerizable substrate having a radical-polymerizable terminal group and/or radical generating group, wherein the polymerizable substrate is the base material (such as a crosslinking agent as described herein), or can be engrafted to or otherwise affixed to the base material (such as the substrate), thereby substantially taking the form of the base material. The polymeric chain can be formed from any polymerizable macromer. Polymer brushes are formed by radical polymerization as described below. A brush has an elongated shape of a particular size in one direction related to the degree of polymerization in a first direction, its "length", and a cross sectional diameter or thickness is related to the degree of polymerization in a second direction perpendicular to the first direction, its "width". The brushes can assume a coiled or compacted morphology or an extended morphology. The width of a brush can vary along its length. In addition, the polymerization reaction can be controlled to create branch-like polymer brush structures, as well as increasing or decreasing brush density, i.e., number of brushes per surface area or per weight of base material, as described below. The length, width, branching, and overall morphology of the polymer brushes in the present invention can be varied according to the desired end use or purpose as described herein and by methods known in the art.

"Protecting group" is a group that is appended to, for example, a hydroxyl oxygen in place of a labile hydrogen atom. Suitable hydroxyl protecting group(s) include esters (acetate, ethylacetate), ethers (methyl, ethyl), ethoxylated derivatives (ethylene glycol, propylene glycol) and the like that can be removed under either acidic or basic conditions so that the protecting group is removed and replaced with a hydrogen atom. Guidance for selecting appropriate protecting groups, as well as synthetic strategies for their attachment and removal, may be found, for example, in Greene & Wuts, *Protective Groups in Organic Synthesis*, 3d Edition, John Wiley & Sons, Inc., New York (1999) and the references cited therein (hereinafter "Greene & Wuts").

Alternatively, the compositions of the invention can be solubilized in water/alcohol solutions or in alcohols, such as isopropanol, butanol, methanol, ethanol, cellosolves (glycols), ketones, (e.g., acetone), carboxylic esters (e.g., ethyl acetate) and the like.

Examples of moieties that help to provide hydrophilicity to the compositions of the invention are as described above and include hydroxyl groups, polyhydric groups, alkoxy groups, polyoxyalkylenes, amines, amides, esters and ionic groups.

Once the composition is applied to a substrate, the coating can then be subjected to an energy source suitable to initiate reaction of the initiator and/or the crosslinker.

The compositions of the invention can be applied to a surface of interest in any suitable manner. For example, the composition can be applied by dip coating or by dispersing the compound on the surface (for example, by spray coating). Suitable methods of application include application in solution, dipping, spray coating, knife coating, and roller coating. In one aspect, the composition is applied to the surface via spray coating, as this application method provides increased control of the density of the coating on the support surface, thereby improving durability.

Generally the thickness of the coatings of the invention are between about 2 nanometers (nm) and about 1000 microns, in particular between about 5 nm and about 200 nm and most particularly between about 20 nm and about 100 nm.

Not to be limited by theory, the coatings of the invention adhere to the surface of the substrate. It is unknown whether the adhesion is from covalent or ionic attachment, or if any physical attachment actually occurs. However, it has been found that treatment of the coatings where inter- or intrapolymeric crosslinking is accomplished (such as thermal, photoactivation (photopolymerization), radical generation, etc.) often provides a durable coating that is not easily removed.

Plastics such as polyolefins (such as ultra-high molecular weight polyethylene, UHMWPE), polystyrenes, poly(methyl)methacrylates, polyacrylonitriles, poly(vinylacetates), poly (vinyl alcohols), chlorine-containing polymers such as poly(vinyl) chloride, polyoxymethylenes, polycarbonates, polyamides, polyimides, polyurethanes, phenolics, amino-epoxy resins, polyesters, silicones, cellulose-based plastics, and rubber-like plastics can all be used as supports, providing surfaces that can be modified as described herein. See generally, "Plastics", pp. 462-464, in Concise Encyclopedia of Polymer Science and Engineering, Kroschwitz, ed., John Wiley and Sons, 1990, the disclosure of which is incorporated herein by reference. In addition, supports such as those formed of pyrolytic carbon, parylene coated surfaces, and silylated surfaces of glass, ceramic, natural polymers, such as wood (cellulose), polysaccharides, proteins, paper, ceramics, metals or composites are suitable for surface modification.

The coating provided by the compositions of the invention provide improved surface characteristics, such as lubricity or function to reduce friction when contacted to a second surface, such as in artificial joints and medical devices.

Photoactivation can be defined as a phenomenon whereby individual substances are joined together to create a new larger structure by way of the action of light. When light is absorbed, electrons populate excited states in molecules. These excited states are generally quite short-lived and terminate by one of three pathways. The excited state can emit a photon from either a singlet state (fluorescence) or a triplet state (phosphorescence), lose its energy via vibrations in the form on heat, or react chemically. Because the absorption of a photon highly excites a molecule, there is a much wider variety of reactions possible than standard thermochemical means. Photocrosslinking uses these reactions to join small molecules to other small molecules, large molecules to small molecules, and large molecules to each other (photocoupling of polymers), as well as large and small molecules to substrates or particles (photobonding to surfaces). During photocrosslinking each increase in molecular weight is initiated by its own photochemical reaction and the coupling of radicals can result in the formation of crosslinks, especially in the solid state. Photocrosslinking can usually be classified into two types.

The first type is where crosslinks are formed by the direct reaction of an excited molecule. Representative reactions would be a photo 2+2 cycloaddition (or 4+4) and cis-trans isomerization of double bonds. Examples of this type are demonstrated by the cyclodimerization of cinnamic acid and derivatives, chalcones and stilbenes, anthracenes, maleimides and strained cycloalkenes. In another large class of reactions, the triplet, $T_1$ excited state of carbonyl groups in ketones can result in either fragmentation (Norrish Type I reaction) or hydrogen abstraction (Norrish type II reaction).

Both of these photoreactions create two radicals which can then subsequently react with surrounding molecules. For example, aromatic ketones, such as benzophenone, readily undergo hydrogen abstraction reactions with any preformed polymer possessing C—H bonds. A possible mechanism is shown in the Scheme which follows.

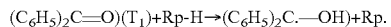

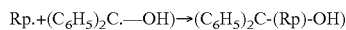

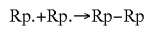

The second usual type of photocrosslinking is where crosslinks occur through the action of a photogenerated reactive species. Examples of the second type include the use of nitrenes that are formed from organic azides, and carbenes.

Whether through direct excited state reaction or reactive intermediates, photolysis of photoreactive groups can begin a process of bond formation throughout a mixture. The act of cross linking will serve to increase the durability of this surface. Bonds will be formed between initiators and crosslinkers, crosslinkers and crosslinkers, initiators and initiators, and between crosslinkers and/or initiators and the surface of the substrate. Bond formation may take place by many means within the various systems. In many cases radicals are formed through photolysis. Radicals can form new bonds through radical-radical recombination, addition to unsaturated bonds, hydrogen abstraction and subsequent recombination or addition, further fragmentation, oxygen addition, or disproportionation, as well as possible electron transfer reactions. Similarly, photoreactive polymeric species can be bonded to the surface of the substrate. These newly formed covalent bonds increase the durability and stability of the matrix. In cases which generate carbenes and nitrenes, bonds would be formed typically by insertion, hydrogen abstraction to form radicals, rearrangements, etc. This invention is not limited to these mechanisms, and in fact, many mechanisms may be at work within one photoactivatable crosslinker(s) and initiator(s) system.

Photoreactive species are as described herein, and are sufficiently stable to be stored under conditions in which they retain such properties. See, e.g., U.S. Pat. No. 5,002,582, the disclosure of which is incorporated herein by reference. Latent reactive groups can be chosen that are responsive to various portions of the electromagnetic spectrum, with those responsive to ultraviolet, infrared and visible portions of the spectrum (referred to herein as "photoreactive").

Latent reactive groups respond to external stimuli and undergo active specie generation with the formation of a covalent bond to an adjacent chemical structure, e.g., as provided by the same or a different molecule. Latent reactive groups are those groups of atoms in a molecule that retain their covalent bonds during storage but, upon activation by an external energy source, form covalent bonds with other molecules.

Photoreactive groups generate active species such as free radicals and particularly nitrenes, carbenes, and excited states of ketones upon absorption of electromagnetic energy. Photoreactive groups can be chosen to be responsive to various portions of the electromagnetic spectrum, and photoreactive species that are responsive to electromagnetic radiation, including, but not limited to ultraviolet, infrared and visible portions of the spectrum, are referred to as a "photochemical group" or "photogroup."

The initiators that can be combined with the crosslinkers described herein to form the inventive compositions of the invention include photoreactive initiators as well as thermal initiators.

Free radical initiators can be classified by the following two types.

Type A. Compounds directly produce radicals by unimolecular fragmentation after external energy absorption. The radicals result from a homolytic or heterolytic cleavage of a sigma bond inside the molecule itself. Common examples include but are not limited to peroxides, and peroxy compounds, benzoin derivatives (including ketoxime esters of benzoin), acetophenone derivatives, benzilketals, α-hydroxyalkylphenones and α-aminoalkylphenones, O-acyl α-oximinoketones, acylphosphine oxides and acylphosphonates, thiobenzoic S-esters, azo and azide compounds, triazines and biimidazoles.

Type B. Compounds generate free radicals by bimolecular hydrogen abstraction after light absorption. The hydrogen abstraction photoreactive group enters an excited state and undergo an intermolecular reaction with a hydrogen donor to generate free radicals. This leads to the formation of a pair of radicals originating from two different molecules. The coupling of radicals can be used to form crosslinks, especially in the solid state in the absence of solvents. Common examples include but are not limited to the following chemical classes. Quinones, benzophenones, xanthones and thioxanthones, ketocoumarins, aromatic 1,2 diketones and phenylglyoxylates. Hydrogen abstraction reactions can also occur intramolecularly. The reactions are not effective for the direct initiation of polymerization and are used internally for the formation of an intermediate. This intermediate may be effective for further cross linking depending on its structure.

The photolysis of organic azides has been shown to result in $N_2$ loss, producing nitrenes as reactive intermediates. Nitrenes are known to undergo five general reactions. 1) Addition to double bonds is observed for both singlet and triplet nitrenes which in the case of arylnitrenes results in rearrangement of the aziridine to a secondary amine as a conceivable mechanism. 2) Insertion of a nitrene into a carbon-hydrogen bond to give a secondary amine which is observed for singlet nitrenes. 3) Hydrogen abstraction is the most common reaction of triplet nitrenes in solution where the formed amino radical and carbon radical generally diffuse apart and the amino radical abstracts a second hydrogen atom to give a primary amine. 4) Nitrene dimerization 5) Attack on heteroatom, for example nitrenes react with azides and oxygen.

Upon direct excitation, carbon halogen bonds such as those in trichloromethyl triazine, tribromomethyl triazine, and aryl iodides, homolytically cleave forming a halogen radical and a carbon radical. Either or both radicals can then abstract hydrogen, disproportionate, couple other radicals, add to unsaturated bonds, or perform other typical radical reactions resulting in crosslinking and bond formation. Suitable examples include trichloromethyl triazines, tribromomethyl triazines and/or aryl iodides.

The use of photoreactive groups in the form of photoreactive aryl ketones are useful such as acetophenone, benzophenone, anthraquinone, anthrone, and anthrone-like heterocycles (i.e., heterocyclic analogs of anthrone such as those having N, O, or S in the 10-position), or their substituted (e.g., ring substituted) derivatives. Examples of aryl ketones include heterocyclic derivatives of anthrone, including acridone, xanthone, and thioxanthone, and their ring substituted derivatives. In particular, thioxanthone, and its derivatives, having excitation wavelengths greater than about 360 nm are useful.

The photoreactive groups of such ketones are preferred since they are readily capable of undergoing an activation/inactivation/reactivation cycle. Benzophenone, acetophenone and anthraquinone are examples of photoreactive moieties, since they are capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (e.g., carbon-hydrogen) is not available for bonding, the ultraviolet light-induced excitation of the benzophenone, acetophenone or anthraquinone group is reversible and the molecule returns to ground state energy level upon removal of the energy source. Photoactivatable aryl ketones such as benzophenone, anthraquinone and acetophenone are of particular importance inasmuch as these groups are subject to multiple reactivation in water and hence provide increased coating efficiency.

Another class of photoreactive groups includes compounds having an Si—Si bond, wherein it is believed the Si—Si bond is broken upon excitation with a light source, such as with a laser or UV light. The radicals generated upon the bond breakage provide for reactive sites suitable for use with the present invention. (For examples of Si—Si bond cleavage, see J. Lalevee, M. El-Roz, F. Morlet-Savery, B. Graff, X. Allonas and J. P. Fouassier, "New Highly efficient Radical Photoinitiators based on Si—Si Cleavage" Macromolecules, 2007, 40, 8527-8530 which describes 10, 10'-bis (10-phenyl-10H-phenoxasilin (Sigma-Aldrich, St. Louis Mo.) and 9,9'-dimethyl-9,9'-bis-(9H-9-silafluorene, the contents of which are incorporated herein in their entirety.)

Thermal polymerization can be defined as a phenomenon whereby individual substances are joined together to create larger structures by the action of heat. Numerous substances decompose to free radicals when heated. If the decomposition temperature corresponds to a convenient temperature range the substance may be useful in reactions to join small molecules to other small molecules, large molecules to small molecules and large molecules to each other (thermal coupling of polymers), as well as large and small molecules to substrates or particles (thermal bonding to surfaces). Useful thermal initiators include organic peroxides, redox reagents, organic hydroperoxides, azo compounds, metal alkyls and organometallic reagents.

Dialkyl, diacyl and hydrogen peroxides decompose thermally by cleavage of the oxygen bond to yield two alkoxy radicals. Azo compounds decompose thermally to give nitrogen and two alkyl radicals. The radicals may then initiate reactions as described in photopolymerization free radical reactions.

Medical articles that can be fabricated from or coated or treated with the compositions of the invention include, but are not limited to, catheters including urinary catheters and vascular catheters (e.g., peripheral and central vascular catheters), wound drainage tubes, arterial grafts, soft tissue patches, gloves, shunts, stents, tracheal catheters, wound dressings, sutures, guide wires, prosthetic devices (e.g., heart valves and LVADs) and artificial joints, such as implants (knee, hip, cervical, vertebral, etc.). Vascular catheters which can be prepared according to the present invention include, but are not limited to, single and multiple lumen central venous catheters, peripherally inserted central venous catheters, emergency infusion catheters, percutaneous sheath introducer systems, thermodilution catheters, including the hubs and ports of such vascular catheters, leads to electronic devices such as pacemakers, defibrillators, artificial hearts, and implanted biosensors.

In another embodiment, the compounds of the invention can be applied to a microscope slide or "chip" for biomolecule immobilization.

The following paragraphs enumerated consecutively from one (1) through 80 provide for various aspects of the present invention. In one embodiment, in a first paragraph (1), the present invention provides a composition comprising a formula:

wherein L is a linking group;

D is O, S, SO, $SO_2$, $NR^5$ or $CR^6R^7$;

T is $(-CH_2-)_x$, $(-CH_2CH_2-O-)_x$, $(-CH_2CH_2CH_2-O-)_x$, $(-CH_2CH_2CH_2CH_2-O-)_x$ or forms a bond;

$R^1$ is a hydrogen atom, an alkyl, alkyloxyalkyl, aryl, aryloxyalkyl or aryloxyaryl group;

X is O, S, or $NR^8R^9$;

P is a hydrogen atom or a protecting group, with the proviso that P is absent when X is $NR^8R^9$;

$R^2$ is a hydrogen atom, an alkyl, alkyloxyalkyl, aryl, aryloxyalkyl or aryloxyaryl group;

G is O, S, SO, $SO_2$, $NR^{10}$, $(CH_2)_r$—O— or C=O;

$R^3$ and $R^4$ are each independently an alkyl, aryl, arylalkyl, heteroaryl, or an heteroarylalkyl group or optionally, $R^3$ and $R^4$ can be tethered together via $(-CH_2-)_q$, $(-CH_2-)_r$C=O$(-CH_2-)_s$, $(-CH_2-)_r$S$(-CH_2-)_s$, $(-CH_2-)_r$=O$(-CH_2-)_s$ or $(-CH_2-)_r$S(O)$_2$$(-CH_2-)_s$, $(-CH_2-)_r$NR$(-CH_2-)_s$;

$R^5$ and $R^{10}$ are each independently a hydrogen atom or an alkyl, aryl or arylalkyl group;

$R^6$ and $R^7$ are each independently a hydrogen atom, an alkyl, aryl, arylalkyl, heteroaryl or heteroarylalkyl group;

$R^8$ and $R^9$ are each independently a hydrogen atom, an alkyl, aryl, or arylalkyl group;

R is a hydrogen atom, an alkyl or an aryl group;

q is an integer from 1 to about 7;

r is an integer from 0 to about 3;

s is an integer from 0 to about 3;

m is an integer from 2 to about 10;

t is an integer from 1 to about 10;

x is an integer from 1 to about 500; and a polymerizable monomer.

2. The composition according to paragraph 1, wherein L is

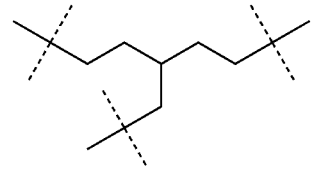

D is O, T is $(-CH_2-)_x$, $R^1$ is a hydrogen atom, X is O, P is a hydrogen atom, $R^2$ is a hydrogen atom, G is O, $R^3$ and $R^4$ are phenyl groups, m is 3 and x is 1.

3. The composition according to paragraph 1, wherein L is $(-CH_2-)_y$, D is O, T is $(-CH_2-)_x$, $R^1$ is a hydrogen atom, X is O, P is a hydrogen atom, $R^2$ is a hydrogen atom, G is O, $R^3$ and $R^4$ are phenyl groups, m is 2, x is 1 and y is an integer from 2 to about 6.

4. A composition comprising a formula:

wherein L is a linking group;

T is $(-CH_2-)_x$, $(-CH_2CH_2-O-)_x$, $(-CH_2CH_2CH_2-O-)_x$, $(-CH_2CH_2CH_2CH_2-O-)$, or forms a bond;

$R^1$ is a hydrogen atom, an alkyl, alkyloxyalkyl, aryl, aryloxyalkyl or aryloxyaryl group;

X is O, S, or $NR^8R^9$;

P is a hydrogen atom or a protecting group, with the proviso that P is absent when X is $NR^8R^9$;

$R^2$ is a hydrogen atom, an alkyl, alkyloxyalkyl, aryl, aryloxylalkyl or aryloxyaryl group;

G is O, S, SO, $SO_2$, $NR^{10}$, $(CH_2)_t$—O— or C=O;

$R^3$ and $R^4$ are each independently an alkyl, aryl, arylalkyl, heteroaryl, or an heteroarylalkyl group, or optionally, $R^3$ and $R^4$ can be tethered together via $(-CH_2-)_q$, $(-CH_2-)_r$ C=O$(-CH_2-)_s$, $(-CH_2-)_rS(-CH_2-)_s$, $(-CH_2-)_r$ S=O$(-CH_2-)_s$ or $(-CH_2-)_rS(O)_2(-CH_2-)_s$, $(-CH_2-)_rNR(-CH_2-)_s$;

$R^{10}$ is a hydrogen atom or an alkyl, aryl or arylalkyl group;

$R^8$ and $R^9$ are each independently a hydrogen atom, an alkyl, aryl, or arylalkyl group;

R is a hydrogen atom, an alkyl or aryl group;

q is an integer from 1 to about 7;

r is an integer from 0 to about 3;

s is an integer from 0 to about 3;

m is an integer from 2 to about 10;

t is an integer from 1 to about 10;

x is an integer from 1 to about 500; and a polymerizable monomer.

5. The composition of paragraph 4, wherein L has a formula according to structure (I):

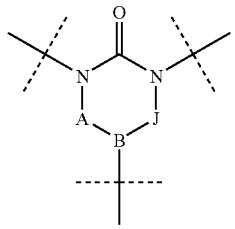

(I)

wherein A and J are each independently a hydrogen atom, an alkyl group, an aryl group, or together with B form a cyclic ring, provided when A and J are each independently a hydrogen atom, an alkyl group, or an aryl group then B is not present;

B is $NR^{11}$, O, or $(-CH_2-)_z$;

provided when A, B and J form a ring, then A and J are $(-CH_2-)_z$ or C=O;

$R^{11}$ is a hydrogen atom, an alkyl group, an aryl group or denotes a bond with T;

each z independently is an integer from 0 to 3; and provided when either A or J is C=O, then B is $NR^{11}$, O, or $(-CH_2-)_z$ and z must be at least 1.

6. A composition comprising a formula:

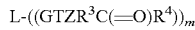

L-((GTZR$^3$C(=O)R$^4$))$_m$ wherein L is a linking group;

T is $(-CH_2-)_x$, $(-CH_2CH_2-O-)_x$, $(-CH_2CH_2CH_2-O-)_x$, $(-CH_2CH_2CH_2CH_2-O-)_x$ or forms a bond;

G is O, S, SO, $SO_2$, $NR^{10}$, $(CH_2)_t$—O— or C=O;

Z is C=O, COO, or CONH when T is $(-CH_2-)_x$;

$R^3$ and $R^4$ are each independently an alkyl, aryl, arylalkyl, heteroaryl, or an heteroarylalkyl group, or optionally, $R^3$ and $R^4$ can be tethered together via $(-CH_2-)_q$, $(-CH_2-)_r$ C=O$(-CH_2-)_s$, $(-CH_2-)_rS(-CH_2-)_s$, $(-CH_2-)_r$ S=O$(-CH_2-)_s$ or $(-CH_2-)_rS(O)_2(-CH_2-)_s$, $(-CH_2-)_rNR(-CH_2-)_s$;

$R^{10}$ is a hydrogen atom or an alkyl, aryl, or an arylalkyl group;

R is a hydrogen atom or an alkyl or aryl group;

q is an integer from 1 to about 7;

r is an integer from 0 to about 3;

s is an integer from 0 to about 3;

m is an integer from 2 to about 10;

t is an integer from 1 to about 10;

x is an integer from 1 to about 500; and a polymerizable monomer.

7. The composition of paragraph 6, wherein L has a formula according to structure (I):

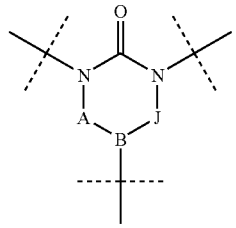

wherein A and J are each independently a hydrogen atom, an alkyl group, an aryl group, or together with B form a cyclic ring, provided when A and J are each independently a hydrogen atom, an alkyl group, or an aryl group then B is not present;

B is $NR^{11}$, O, or $(-CH_2-)_z$;

provided when A, B and J form a ring, then A and J are $(-CH_2-)_z$ or C=O;

$R^{11}$ is a hydrogen atom, an alkyl group, an aryl group or denotes a bond with T each z independently is an integer from 0 to 3; and provided when either A or J is C=O, then B is $NR^{11}$, O, or $(-CH_2-)_z$, and z must be at least 1.

8. The composition of paragraph 6, wherein L has a formula according to structure (II):

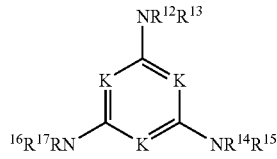

(II)

wherein $R^{12}$, $R^{13}$, $R^{14}$, $R^{15}$, $R^{16}$, $R^{17}$ are each independenly a hydrogen atom, an alkyl or aryl group or denotes a bond with T, provided at least two of $R^{12}$, $R^{13}$, $R^{14}$, $R^{15}$, $R^{16}$, $R^{17}$ are bonded with T and each K, independently, is CH or N.

9. A composition comprising a formula:

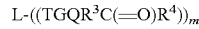

L-((TGQR$^3$C(=O)R$^4$))$_m$ wherein L is a linking group;

T is $(-CH_2-)_x$, $(-CH_2CH_2-O-)_x$, $(-CH_2CH_2CH_2-O-)_x$, $(-CH_2CH_2CH_2CH_2-O-)_x$ or forms a bond;

G is O, S, SO, $SO_2$, $NR^{10}$, $(CH_2)_t$—O— or C=O;

Q is $(-CH_2-)_p$, $(-CH_2CH_2-O-)_p$, $(-CH_2CH_2CH_2-O-)_p$ or $(-CH_2CH_2CH_2CH_2-O-)_p$;

R$^3$ and R$^4$ are each independently an alkyl, aryl, arylalkyl, heteroaryl, or an heteroarylalkyl group, or optionally, R$^3$ and R$^4$ can be tethered together via (—CH$_2$—)$_q$, C=O(—CH$_2$—)$_s$, (—CH$_2$—)$_r$S(—CH$_2$—)$_s$, (—CH$_2$—)$_r$S=O(—CH$_2$—)$_s$ or (—CH$_2$—)$_r$S(O)$_2$(—CH$_2$—)$_s$, (—CH$_2$—)$_r$NR(—CH$_2$—)$_s$;

R$^{10}$ is a hydrogen atom or an alkyl, aryl, or an arylalkyl group;

R is a hydrogen atom or an alkyl or aryl group;

q is an integer from 1 to about 7;

r is an integer from 0 to about 3;

s is an integer from 0 to about 3;

m is an integer from 2 to about 10;

p is an integer from 1 to about 10;

t is an integer from 1 to about 10;

x is an integer from 1 to about 500; and a polymerizable monomer.

10. The composition of paragraph 9, wherein L has a formula according to structure (I):

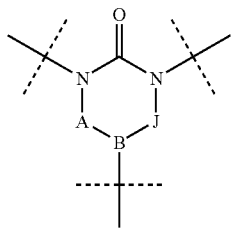

wherein A and J are each independently a hydrogen atom, an alkyl group, an aryl group, or together with B form a cyclic ring, provided when A and J are each independently a hydrogen atom, an alkyl group, or an aryl group then B is not present;

B is NR$^{11}$, O, or (—CH$_2$—)$_z$;

provided when A, B and J form a ring, then A and J are (—CH$_2$—)$_z$ or C=O;

R$^{11}$ is a hydrogen atom, an alkyl group, an aryl group or denotes a bond with T each z independently is an integer from 0 to 3; and provided when either A or J is C=O, then B is NR$^{11}$, O, or (—CH$_2$—)$_z$. and z must be at least 1.

11. The composition of paragraph 9, wherein L has a formula according to structure (II):

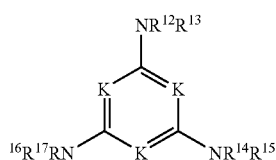

(II)

wherein R$^{12}$, R$^{13}$, R$^{14}$, R$^{15}$, R$^{16}$, R$^{17}$ are each independently a hydrogen atom, an alkyl or aryl group or denotes a bond with T, provided at least two of R$^{12}$, R$^{13}$, R$^{14}$, R$^{15}$, R$^{16}$, R$^{17}$ are bonded with T and each K, independently, is CH or N.

12. A composition comprising a formula:

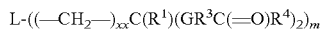

wherein L is a linking group;

R$^1$ is a hydrogen atom, an alkyl, alkyloxyalkyl, aryl, aryloxyalky, or aryloxyaryl group;

each G is O, S, SO, SO$_2$, NR$^{10}$, (CH$_2$)$_t$—O— or C=O;

each R$^3$ and R$^4$ are each independently an alkyl, aryl, arylalkyl, heteroaryl, or an heteroarylalkyl group, or optionally, R$^3$ and R$^4$ can be tethered together via (—CH$_2$—)$_q$, (—CH$_2$—)$_r$C=O(—CH$_2$—)$_s$, (—CH$_2$—)$_r$S(—CH$_2$—)$_s$, (—CH$_2$—)$_r$S=O(—CH$_2$—)$_s$ or (—CH$_2$—)$_r$S(O)$_2$(—CH$_2$—)$_s$, (—CH$_2$—)$_r$NR(—CH$_2$—)$_s$;

each R$^{10}$ is a hydrogen atom or an alkyl, aryl, or an arylalkyl group;

each R is a hydrogen atom or an alkyl or aryl group;

each q is an integer from 1 to about 7;

each r is an integer from 0 to about 3;

each s is an integer from 0 to about 3;

m is an integer from 2 to about 10;

each t is an integer from 1 to about 10;

xx is an integer from 1 to about 10; and a polymerizable monomer.

13. The composition of paragraph 12, wherein L has a formula according to structure (I):

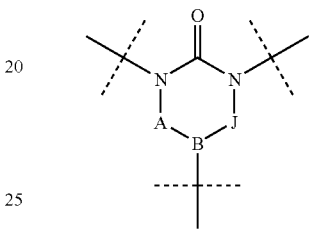

wherein A and J are each independently a hydrogen atom, an alkyl group, an aryl group, or together with B form a cyclic ring, provided when A and J are each independently a hydrogen atom, an alkyl group, or an aryl group then B is not present;

B is NR$^{11}$, O, or (—CH$_2$—)$_z$;

provided when A, B and J form a ring, then A and J are (—CH$_2$—)$_z$ or C=O;

R$^{11}$ is a hydrogen atom, an alkyl group, an aryl group or denotes a bond with T each z independently is an integer from 0 to 3; and provided when either A or J is C=O, then B is NR$^{11}$, O, or (—CH$_2$—)$_z$. and z must be at least 1.

14. The composition of paragraph 13, wherein A and B are both hydrogen atoms.

15. The composition of paragraph 14, wherein xx is 1, each G is (—CH$_2$—)$_t$O— and t is 1, each R$^1$ is H and each R$^3$ and R$^4$ are each individually aryl groups.

16. A composition comprising a formula:

wherein L is a linking group;

R$^1$ is a hydrogen atom, an alkyl, alkyloxyalkyl, aryl, aryloxyalkyl or aryloxyaryl group;

X is O, S, or NR$^8$R$^9$;

P is a hydrogen atom or a protecting group, with the proviso that P is absent when X is NR$^8$R$^9$;

R$^2$ is a hydrogen atom, an alkyl, alkyloxyalkyl, aryl, aryloxyalkyl or aryloxyaryl group;

G is O, S, SO, SO$_2$, NR$^{10}$, (CH$_2$)$_t$—O— or C=O;

R$^3$ and R$^4$ are each independently an alkyl, aryl, arylalkyl, heteroaryl, or an heteroarylalkyl group, or optionally, R$^3$ and R$^4$ can be tethered together via (—CH$_2$—)$_q$, (—CH$_2$—)$_r$C=O(—CH$_2$—)$_s$, (—CH$_2$—)$_r$S(—CH$_2$—)$_s$, (—CH$_2$—)$_r$S=O(—CH$_2$—)$_s$ or (—CH$_2$—)$_r$S(O)$_2$(—CH$_2$—)$_s$, (—CH$_2$—)$_r$NR(—CH$_2$—)$_s$;

R$^8$ and R$^9$ are each independently a hydrogen atom, an alkyl, aryl, or arylalkyl group;

R$^{10}$ is a hydrogen atom or an alkyl, aryl, or an arylalkyl group;

R is a hydrogen atom, an alkyl or an aryl group;
q is an integer from 1 to about 7;
r is an integer from 0 to about 3;
s is an integer from 0 to about 3;
m is an integer from 2 to about 10;
t is an integer from 1 to about 10; and
a polymerizable monomer.

17. The composition of paragraph 16, wherein L is

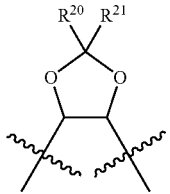

and $R^{20}$ and $R^{21}$ are each individually a hydrogen atom, an alkyl group or an aryl group.

18. The composition of paragraph 17, wherein $R^1$ is H, X is O, P is H, $R^2$ is H, G is (—CH$_2$—)$_t$O—, t is 1, $R^3$ and $R^4$ are each individually aryl groups and $R^{20}$ and $R^{21}$ are both methyl groups.

19. A composition comprising the formula:

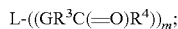

wherein L is a linking group;
G is O, S, SO, SO$_2$, NR$^{10}$, (CH$_2$)$_t$—O— or C=O;
$R^3$ and $R^4$ are each independently an alkyl, aryl, arylalkyl, heteroaryl, or an heteroarylalkyl group, or optionally, $R^3$ and $R^4$ can be tethered together via (—CH$_2$—)$_q$, (—CH$_2$—)$_r$C=O(—CH$_2$—)$_s$, (—CH$_2$—)$_r$S(—CH$_2$—)$_s$, (—CH$_2$)$_r$S=O(—CH$_2$—)$_s$ or (—CH$_2$—)$_r$S(O)$_2$(—CH$_2$—)$_s$, (—CH$_2$—)$_r$—NR(—CH$_2$—)$_s$;
$R^{10}$ is a hydrogen atom or an alkyl, aryl, or an arylalkyl group;
R is a hydrogen atom, an alkyl or an aryl group;
q is an integer from 1 to about 7;
r is an integer from 0 to about 3;
s is an integer from 0 to about 3;
m is an integer from 2 to about 10;
t is an integer from 1 to about 10; and
a polymerizable monomer.

20. The composition of paragraph 19, wherein L is

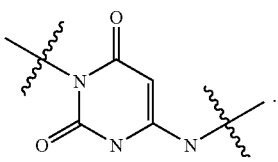 [SMILES: *Nc1cc(=O)n(*)c(=O)[nH]1]

21. A composition comprising a formula:

wherein L is (—OCH$_2$CH$_2$O—)$_{qq}$;
T is (—CH$_2$—)$_x$;
$R^1$ is a hydrogen atom, an alkyl, alkyloxyalkyl, aryl, aryloxyalkyl or aryloxyaryl group;
X is O, S, or NR$^8$R$^9$;
P is a hydrogen atom or a protecting group, with the proviso that P is absent when X is NR$^8$R$^9$;
$R^2$ is a hydrogen atom, an alkyl, alkyloxyalkyl, aryl, aryloxylalkyl or aryloxyaryl group;
G is O, S, SO, SO$_2$, NR$^{10}$, (CH$_2$)$_t$—O— or C=O;
$R^3$ and $R^4$ are each independently an alkyl, aryl, arylalkyl, heteroaryl, or an heteroarylalkyl group, or optionally, $R^3$ and $R^4$ can be tethered together via (—CH$_2$—)$_q$, (—CH$_2$—)$_r$C=O(—CH$_2$—)$_s$, (—CH$_2$—)$_r$S(—CH$_2$—)$_s$, (—CH$_2$—)$_r$S=O(—CH$_2$—)$_s$ or (—CH$_2$—)$_r$S(O)$_2$(—CH$_2$—)$_s$, (—CH$_2$—)$_r$NR(—CH$_2$—)$_s$;
$R^{10}$ is a hydrogen atom or an alkyl, aryl or arylalkyl group;
$R^8$ and $R^9$ are each independently a hydrogen atom, an alkyl, aryl, or arylalkyl group;
R is a hydrogen atom, an alkyl or aryl group;
q is an integer from 1 to about 7;
r is an integer from 0 to about 3;
s is an integer from 0 to about 3;
m is an integer from 2 to about 10;
t is an integer from 1 to about 10;
x is an integer from 1 to about 500;
qq is an integer from 1 to about 500; and
a polymerizable monomer.

22. The composition of paragraph 21, wherein $R^1$ is H, X is O, P is H, $R^2$ is H, G is O, $R^3$ and $R^4$ are aryl groups, m is 2, x is an integer from 1 to 10 and qq is an integer from 1 to about 10.

23. A method to modify a substrate comprising the step of applying a composition comprising a crosslinker comprising a formula:

wherein L is a linking group;
D is O, S, SO, SO$_2$, NR$^5$ or CR$^6$R$^7$;
T is (—CH$_2$—)$_x$, (—CH$_2$CH$_2$—O—)$_x$, (—CH$_2$CH$_2$CH$_2$—O—)$_x$, (—CH$_2$CH$_2$CH$_2$CH$_2$—O—)$_x$ or forms a bond;
$R^1$ is a hydrogen atom, an alkyl, alkyloxyalkyl, aryl, aryloxyalkyl or aryloxyaryl group;
X is O, S, or NR$^8$R$^9$;
P is a hydrogen atom or a protecting group, with the proviso that P is absent when X is NR$^8$R$^9$;
$R^2$ is a hydrogen atom, an alkyl, alkyloxyalkyl, aryl, aryloxyalkyl or aryloxyaryl group;
G is O, S, SO, SO$_2$, NR$^{10}$, (CH$_2$)$_t$—O— or C=O;
$R^3$ and $R^4$ are each independently an alkyl, aryl, arylalkyl, heteroaryl, or an heteroarylalkyl group or optionally, $R^3$ and $R^4$ can be tethered together via (—CH$_2$—)$_q$, (—CH$_2$—)$_r$C=O(—CH$_2$—)$_s$, (—CH$_2$—)$_r$S(—CH$_2$—)$_s$, (—CH$_2$)$_r$S=O(—CH$_2$—)$_s$ or (—CH$_2$—)$_r$S(O)$_2$(—CH$_2$—)$_s$, (—CH$_2$—)$_s$NR(—CH$_2$—)$_s$;
$R^5$ and $R^{10}$ are each independently a hydrogen atom or an alkyl, aryl or arylalkyl group;
$R^6$ and $R^7$ are each independently a hydrogen atom, an alkyl, aryl, arylalkyl, heteroaryl or heteroarylalkyl group;
$R^8$ and $R^9$ are each independently a hydrogen atom, an alkyl, aryl, or arylalkyl group;
R is a hydrogen atom, an alkyl or an aryl group;
q is an integer from 1 to about 7;
r is an integer from 0 to about 3;
s is an integer from 0 to about 3;
m is an integer from 2 to about 10;
t is an integer from 1 to about 10;
x is an integer from 1 to about 500; and
a polymerizable monomer to the surface of the substrate, such that the substrate surface is modified.

24. The method of paragraph 23, wherein the composition is photoactivated such that at least one photoactivatable group within the composition forms a bond with the surface of the substrate.

25. A method to modify a substrate comprising the step of applying a composition comprising a crosslinker comprising a formula:

wherein L is a linking group;

T is (—CH$_2$—)$_x$, (—CH$_2$CH$_2$—O—)$_x$, (—CH$_2$CH$_2$CH$_2$—O)$_x$, (—CH$_2$CH$_2$CH$_2$CH$_2$—O—)$_x$ or forms a bond;

R$^1$ is a hydrogen atom, an alkyl, alkyloxyalkyl, aryl, aryloxyalkyl or aryloxyaryl group;

X is O, S, or NR$^8$R$^9$;

P is a hydrogen atom or a protecting group, with the proviso that P is absent when X is NR$^8$R$^9$;

R$^2$ is a hydrogen atom, an alkyl, alkyloxyalkyl, aryl, arylalkyl or aryloxyaryl group;

G is O, S, SO, SO$_2$, NR$^{10}$, (CH$_2$)$_t$—O— or C=O;

R$^3$ and R$^4$ are each independently an alkyl, aryl, arylalkyl, heteroaryl, or an heteroarylalkyl group, or optionally, R$^3$ and R$^4$ can be tethered together via (—CH$_2$—)$_q$, (—CH$_2$—)$_r$C=O(—CH$_2$—)$_s$, (—CH$_2$—)$_r$S(—CH$_2$—)$_s$, (—CH$_2$—)$_r$S=O(—CH$_2$—)$_s$ or (—CH$_2$—)$_r$S(O)$_2$(—CH$_2$—)$_s$, (—CH$_2$—)$_r$NR(—CH$_2$—)$_s$;

R$^{10}$ is a hydrogen atom or an alkyl, aryl or arylalkyl group;

R$^8$ and R$^9$ are each independently a hydrogen atom, an alkyl, aryl, or arylalkyl group;

R is a hydrogen atom, an alkyl or aryl group;

q is an integer from 1 to about 7;

r is an integer from 0 to about 3;

s is an integer from 0 to about 3;

m is an integer from 2 to about 10;

t is an integer from 1 to about 10;

x is an integer from 1 to about 500; and a polymerizable monomer to the surface of the substrate, such that the substrate surface is modified.

26. The method of paragraph 25, wherein the composition is photoactivated such that at least one photoactivatable group within the composition forms a bond with the surface of the substrate.

27. A method to modify a substrate comprising the step of applying a composition comprising a crosslinker comprising a formula:

L-((GTZR$^3$C(=O)R$^4$))$_m$ wherein L is a linking group;

T is (—CH$_2$—)$_x$, (—CH$_2$CH$_2$—O—)$_x$, (—CH$_2$CH$_2$CH$_2$—O—)$_x$, (—CH$_2$CH$_2$CH$_2$CH$_2$—O—)$_x$ or forms a bond;

G is O, S, SO, SO$_2$, NR$^{10}$, (CH$_2$)$_t$—O— or C=O;

Z is C=O, COO, or CONH when T is (—CH$_2$—)$_x$;

R$^3$ and R$^4$ are each independently an alkyl, aryl, arylalkyl, heteroaryl, or an heteroarylalkyl group, or optionally, R$^3$ and R$^4$ can be tethered together via (—CH$_2$—)$_q$, (—CH$_2$—)$_r$C=O(—CH$_2$—)$_s$, (—CH$_2$—)$_r$S(—CH$_2$—)$_s$, (—CH$_2$—)$_r$S=O(—CH$_2$—)$_s$ or (—CH$_2$—)$_r$S(O)$_2$(—CH$_2$—)$_s$, (—CH$_2$—)$_r$NR(—CH$_2$—)$_s$;

R$^{10}$ is a hydrogen atom or an alkyl, aryl, or an arylalkyl group;

R is a hydrogen atom or an alkyl or aryl group;

q is an integer from 1 to about 7;

r is an integer from 0 to about 3;

s is an integer from 0 to about 3;

m is an integer from 2 to about 10;

t is an integer from 1 to about 10;

x is an integer from 1 to about 500; and a polymerizable monomer to the surface of the substrate, such that the substrate surface is modified.

28. The method of paragraph 27, wherein the composition is photoactivated such that at least one photoactivatable group within the composition forms a bond with the surface of the substrate.

29. A method to modify a substrate comprising the step of applying a composition comprising a crosslinker comprising a formula:

L-((TGQR$^3$C(=O)R$^4$))$_m$ wherein L is a linking group;

T is (—CH$_2$—)$_x$, (—CH$_2$CH$_2$—O—)$_x$, (—CH$_2$CH$_2$CH$_2$—O—)$_x$, (—CH$_2$CH$_2$CH$_2$CH$_2$—O—)$_x$ or forms a bond;

G is O, S, SO, SO$_2$, NR$^{10}$, (CH$_2$)$_t$—O— or C=O;

Q is (—CH$_2$—)$_p$, (—CH$_2$CH$_2$—O—)$_p$, (—CH$_2$CH$_2$CH$_2$—O—)$_p$ or (—CH$_2$CH$_2$CH$_2$CH$_2$—O—)$_p$;

R$^3$ and R$^4$ are each independently an alkyl, aryl, arylalkyl, heteroaryl, or an heteroarylalkyl group, or optionally, R$^3$ and R$^4$ can be tethered together via (—CH$_2$—)$_q$, (—CH$_2$—)$_r$C=O(—CH$_2$—)$_s$, (—CH$_2$—)$_r$S(—CH$_2$—)$_s$, (—CH$_2$—)$_r$S=O(—CH$_2$—)$_s$ or (—CH$_2$—)$_r$S(O)$_2$(—CH$_2$—)$_s$, (—CH$_2$—)$_r$NR(—CH$_2$—)$_s$;

R$^{10}$ is a hydrogen atom or an alkyl, aryl, or an arylalkyl group;

R is a hydrogen atom or an alkyl or aryl group;

q is an integer from 1 to about 7;

r is an integer from 0 to about 3;

s is an integer from 0 to about 3;

m is an integer from 2 to about 10;

p is an integer from 1 to about 10;

t is an integer from 1 to about 10;

x is an integer from 1 to about 500;

a polymerizable monomer to the surface of the substrate, such that the substrate surface is modified.

30. The method of paragraph 29, wherein the composition is photoactivated such that at least one photoactivatable group within the composition forms a bond with the surface of the substrate.

31. A method to modify a substrate comprising the step of applying a composition comprising a crosslinker comprising a formula:

L-((—CH$_2$—)$_{xx}$C(R$^1$)(GR$^3$C(=O)R$^4$)$_2$)$_m$ wherein L is a linking group;

R$^1$ is a hydrogen atom, an alkyl, alkyloxyalkyl, aryl, aryloxyalky, or aryloxyaryl group;

each G is O, S, SO, SO$_2$, NR$^{10}$, (CH$_2$)$_t$—O— or C=O;

each R$^3$ and R$^4$ are each independently an alkyl, aryl, arylalkyl, heteroaryl, or an heteroarylalkyl group, or optionally, R$^3$ and R$^4$ can be tethered together via (—CH$_2$—)$_q$, (—CH$_2$—)$_r$C=O(—CH$_2$—)$_s$, (—CH$_2$—)$_r$S(—CH$_2$—)$_s$, (—CH$_2$—)$_r$S=O(—CH$_2$—)$_s$ or (—CH$_2$—)$_r$S(O)$_2$(—CH$_2$—)$_s$, (—CH$_2$—)$_r$NR(—CH$_2$—)$_s$;

each R$^{10}$ is a hydrogen atom or an alkyl, aryl, or an arylalkyl group;

each R is a hydrogen atom or an alkyl or aryl group;

each q is an integer from 1 to about 7;

each r is an integer from 0 to about 3;

each s is an integer from 0 to about 3;

m is an integer from 2 to about 10;

each t is an integer from 1 to about 10;

xx is an integer from 1 to about 10; and a polymerizable monomer to the surface of the substrate, such that the substrate surface is modified.

32. The method of paragraph 31, wherein the composition is photoactivated such that at least one photoactivatable group within the composition forms a bond with the surface of the substrate.

33. A method to modify a substrate comprising the step of applying a composition comprising a crosslinker comprising a formula:

L-((—C(R$^1$)(XP)CHR$^2$GR$^3$C(=O)R$^4$))$_m$ wherein L is a linking group;

R$^1$ is a hydrogen atom, an alkyl, alkyloxyalkyl, aryl, aryloxyalkyl or aryloxyaryl group;

X is O, S, or NR$^8$R$^9$;

P is a hydrogen atom or a protecting group, with the proviso that P is absent when X is NR$^8$R$^9$;

R$^2$ is a hydrogen atom, an alkyl, alkyloxyalkyl, aryl, aryloxyalkyl or aryloxyaryl group;

G is O, S, SO, SO$_2$, NR$^{10}$, (CH$_2$)$_t$—O— or C=O;

R$^3$ and R$^4$ are each independently an alkyl, aryl, arylalkyl, heteroaryl, or an heteroarylalkyl group, or optionally, R$^3$ and R$^4$ can be tethered together via (CH$_2$—)$_q$, (—CH$_2$—)$_r$C=O(—CH$_2$—)$_s$, (—CH$_2$—)$_r$S(—CH$_2$—)$_s$, (—CH$_2$—)$_r$S=O(—CH$_2$—)$_s$ or (—CH$_2$—)$_r$S(O)$_2$(—CH$_2$—)$_s$, (—CH$_2$—)$_r$NR(—CH$_2$—)$_s$;

R$^8$ and R$^9$ are each independently a hydrogen atom, an alkyl, aryl, or arylalkyl group;

R$^{10}$ is a hydrogen atom or an alkyl, aryl, or an arylalkyl group;

R is a hydrogen atom, an alkyl or an aryl group;

q is an integer from 1 to about 7;

r is an integer from 0 to about 3;

s is an integer from 0 to about 3;

m is an integer from 2 to about 10;

t is an integer from 1 to about 10; and a polymerizable monomer to the surface of the substrate, such that the substrate surface is modified.

34. The method of paragraph 33, wherein the composition is photoactivated such that at least one photoactivatable group within the composition forms a bond with the surface of the substrate.

35. A method to modify a substrate comprising the step of applying a composition comprising a crosslinker comprising a formula:

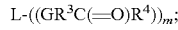

L-((GR$^3$C(=O)R$^4$))$_m$;

wherein L is a linking group;

G is O, S, SO, SO$_2$, NR$^{10}$, (CH$_2$)$_t$—O— or C=O;

R$^3$ and R$^4$ are each independently an alkyl, aryl, arylalkyl, heteroaryl, or an heteroarylalkyl group, or optionally, R$^3$ and R$^4$ can be tethered together via (—CH$_2$—)$_q$, (—CH$_2$—)$_r$C=O(—CH$_2$—)$_s$, (—CH$_2$—)$_r$S(—CH$_2$—)$_s$(—CH$_2$—)$_r$S=O(—CH$_2$—)$_s$ or (—CH$_2$—)$_r$S(O)$_2$(—CH$_2$—)$_s$, (—CH$_2$—)$_r$NR(—CH$_2$—)$_s$;

R$^{10}$ is a hydrogen atom or an alkyl, aryl, or an arylalkyl group;

R is a hydrogen atom, an alkyl or an aryl group;

q is an integer from 1 to about 7;

r is an integer from 0 to about 3;

s is an integer from 0 to about 3;

m is an integer from 2 to about 10;

t is an integer from 1 to about 10; and a polymerizable monomer to the surface of the substrate, such that the substrate surface is modified.

36. The method of paragraph 35, wherein the composition is photoactivated such that at least one photoactivatable group within the composition forms a bond with the surface of the substrate.

37. A method to modify a substrate comprising the step of applying a composition comprising a crosslinker comprising a formula:

L-((T-C(R$^1$)(XP)CHR$^2$GR$^3$C(=O)R$^4$))$_m$ wherein L is (—OCH$_2$CH$_2$O—)$_{qq}$;

T is (—CH$_2$—)$_x$;

R$^1$ is a hydrogen atom, an alkyl, alkyloxyalkyl, aryl, aryloxyalkyl or aryloxyaryl group;

X is O, S, or NR$^8$R$^9$;

P is a hydrogen atom or a protecting group, with the proviso that P is absent when X is NR$^8$R$^9$;

R$^2$ is a hydrogen atom, an alkyl, alkyloxyalkyl, aryl, aryloxyalkyl or aryloxyaryl group;

G is O, S, SO, SO$_2$, NR$^{10}$, (CH$_2$)$_t$—O— or C=O;

R$^3$ and R$^4$ are each independently an alkyl, aryl, arylalkyl, heteroaryl, or an heteroarylalkyl group, or optionally, R$^3$ and R$^4$ can be tethered together via (—CH$_2$—)$_q$, (—CH$_2$—)$_r$C=O(—CH$_2$—)$_s$, (—CH$_2$—)$_r$S(—CH$_2$—)$_s$, (—CH$_2$—)$_r$S=O(—CH$_2$—)$_s$ or (—CH$_2$—)$_r$S(O)$_2$(—CH$_2$—)$_s$, (—CH$_2$—)$_r$NR(—CH$_2$—)$_s$;

R$^{10}$ is a hydrogen atom or an alkyl, aryl or arylalkyl group;

R$^8$ and R$^9$ are each independently a hydrogen atom, an alkyl, aryl, or arylalkyl group;

R is a hydrogen atom, an alkyl or aryl group;

q is an integer from 1 to about 7;

r is an integer from 0 to about 3;

s is an integer from 0 to about 3;

m is an integer from 2 to about 10;

t is an integer from 1 to about 10;

x is an integer from 1 to about 500;

qq is an integer from 1 to about 500; and a polymerizable monomer to the surface of the substrate, such that the substrate surface is modified.

38. The method of paragraph 37, wherein the composition is photoactivated such that at least one photoactivatable group within the composition forms a bond with the surface of the substrate.

39. The compositions or methods of any of paragraphs 1 through 38, wherein the polymerizable monomer has an acrylate, methacrylate, vinyl or diarylketone containing moiety.

40. The composition or method of paragraph 39, wherein the acrylate, methacrylate, vinyl or diarylketone polymerizable polymer further includes a zwitterionic moiety.

41. The composition or method of paragraph 40, wherein the polymerizable monomer is N,N-dimethyl-N-acryloyloxyethyl-N-(3-sulfopropyl)-ammonium betaine, N,N-dimethyl-N-methacryloyloxyethyl-N-(3-sulfopropyl)-ammonium betaine, N,N-dimethyl-N-acrylamidopropyl-N-(2-carboxymethyl)-ammonium betaine, N,N-dimethyl-N-methacrylamidopropyl-N-(2-carboxymethyl)-ammonium betaine, N,N-dimethyl-N-acrylamidopropyl-N-(3-sulfopropyl)-ammonium betaine, N,N-dimethyl-N-methacrylamidopropyl-N-(3-sulfopropyl)-ammonium betaine, N,N-dimethyl-N-acrylamidopropyl-N-(2-carboxymethyl)-ammonium betaine, N,N-dimethyl-N-methacrylamidopropyl-N-(2-carboxymethyl)-ammonium betaine, 2-(methylthio)ethyl methacryloyl-S-(sulfopropyl)-sulfonium betaine, 2-[(2-acryloylethyl)dimethylammonio]ethyl 2-methyl phosphate, 2-(acryloyloxyethyl)-2-(trimethylammonium)ethyl phosphate, [(2-acryloylethyl)dimethylammonio]methyl phosphonic acid, 2-[(3-acrylamidopropyl)dimethylammonio]ethyl 2'-isopropyl phosphate (AAPI), 1-vinyl-3-(3-sulfopropyl)imidazolium hydroxide, (2-acryloxyethyl)carboxymethyl methylsulfonium chloride, 1-(3-sulfopropyl)-2-vinylpyridinium betaine, N-(4-sulfobutyl)-N-methyl-N,N-diallylamine ammonium betaine (MDABS), 2-methacryloyloxyethyl phosphorylcholine, or N,N-diallyl-N-methyl-N-(2-sulfoethyl)ammonium betaine.

42. The composition or method of any of paragraphs 1 through 41, further comprising a photoinitiator or a thermal initiator, wherein the initiator is benzophenone, an acetophenone derivative, a peroxide, a peroxy compound, a benzoin derivative, a benzilketal, a hydroxyalkylphenone, an aminoalkylphenone, an O-acyl oximoketone, an acylphosphine oxides, an acylphosphonate, a thiobenzoic S-ester, an azo or azide compound, a triazine, a 1,2 diketone, a quinone, a coumarins, a xanthone, azobis-isobutyronitrile or a mixture thereof.

43. The method of any of paragraphs 23 through 42, wherein the substrate is polyethylene, polypropylene, nylon, silicone rubber, PVC, polystyrene, polyurethane, glass, cellulose, polysaccharides, proteins, paper, ceramics, metals or composites.

44. The method of any of paragraphs 23 through 42, wherein the crosslinker is applied to the substrate first and subjected to polymerization conditions followed by the polymerizable monomer followed by subsequent polymerization conditions.

45. The method of any of paragraphs 23 through 42, wherein the crosslinker and polymerizable monomer are applied to the substrate and simultaneously subjected to polymerization conditions.

46. A medical device coated with any of the compositions or prepared by any of the methods of any of paragraphs 1 through 45.

47. A composition comprising a diaryl ketone and a zwitterionic monomer.

48. The composition of paragraph 47, wherein the diaryl ketone is acetophenone, benzophenone, anthraquinone, anthrone, acridone, xanthone, thioxanthone, or mixtures thereof.

49. The composition of either of paragraphs 47 or 48, wherein the zwitterionic monomer is N,N-dimethyl-N-acryloyloxyethyl-N-(3-sulfopropyl)-ammonium betaine, N,N-dimethyl-N-methacryloyloxyethyl-N-(3-sulfopropyl)-ammonium betaine, N,N-dimethyl-N-acrylamidopropyl-N-(2-carboxymethyl)-ammonium betaine, N,N-dimethyl-N-methacrylamidopropyl-N-(2-carboxymethyl)-ammonium betaine, N,N-dimethyl-N-acrylamidopropyl-N-(3-sulfopropyl)-ammonium betaine, N,N-dimethyl-N-methacrylamidopropyl-N-(3-sulfopropyl)-ammonium betaine, N,N-dimethyl-N-acrylamidopropyl-N-(2-carboxymethyl)-ammonium betaine, N,N-dimethyl-N-methacrylamidopropyl-N-(2-carboxymethyl)-ammonium betaine, 2-(methylthio)ethyl methacryloyl-S-(sulfopropyl)-sulfonium betaine, 2-[(2-acryloylethyl)dimethylammonio] ethyl 2-methyl phosphate, 2-(acryloyloxyethyl)-2-(trimethylammonium)ethyl phosphate, [(2-acryloylethyl)dimethylammonio]methyl phosphonic acid, 2-[(3-acrylamidopropyl)dimethylammonio]ethyl 2'-isopropyl phosphate (AAPI), 1-vinyl-3-(3-sulfopropyl)imidazolium hydroxide, (2-acryloxyethyl)carboxymethyl methylsulfonium chloride, 1-(3-sulfopropyl)-2-vinylpyridinium betaine, N-(4-sulfobutyl)-N-methyl-N,N-diallylamine ammonium betaine (MDABS), or N,N-diallyl-N-methyl-N-(2-sulfoethyl) ammonium betaine.

50. A method to modify a substrate comprising the step of applying a composition comprising a diaryl ketone and a zwitterionic monomer to the substrate such that the substrate surface is modified.

51. The method of paragraph 50, wherein the diaryl ketone is applied to the substrate first and subjected to polymerization conditions followed by the zwitterionic monomer followed by subsequent polymerization conditions.

52. The method of paragraph 50, wherein the diaryl ketone and zwitterionic monomer are applied to the substrate and simultaneously subjected to polymerization conditions.

53. A medical device coated with any of the compositions or prepared by any of the methods of any of paragraphs 50 through 52.

54. A composition of formula:

L-(D-T-C(R$^1$)(XP)CHR$^2$GR$^3$C(=O)R$^4$)$_m$ wherein L is a linking group comprising a formula according to structure (I):

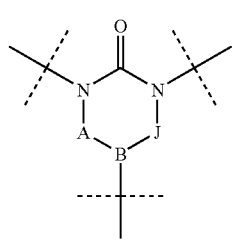

(I)

A, B and J form a ring, wherein A and J are C=O;
B is NR$^{11}$;
R$^{11}$ is a hydrogen atom, an alkyl group, an aryl group or denotes a bond with T or a formula according to structure (II):

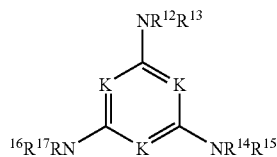

(II)

wherein R$^{12}$, R$^{13}$, R$^{14}$, R$^{15}$, R$^{16}$, R$^{17}$ are each independently a hydrogen atom, an alkyl or aryl group or denotes a bond with T, provided at least two of R$^{12}$, R$^{13}$, R$^{14}$, R$^{15}$, R$^{16}$, R$^{17}$ are bonded with T and each K is N;
D is CR$^6$R$^7$;
T is (—CH$_2$—)$_x$, (—CH$_2$CH$_2$—O—)$_x$, (—CH$_2$CH$_2$CH$_2$—O—)$_x$, (—CH$_2$CH$_2$CH$_2$CH$_2$—O—), or forms a bond;
R$^1$ is a hydrogen atom, an alkyl, alkyloxyalkyl, aryl, aryloxyalkyl or aryloxyaryl group;
X is O, S, or NR$^8$R$^9$;
P is a hydrogen atom or a protecting group, with the provisio that P is absent when X is NR$^8$R$^9$;
R$^2$ is a hydrogen atom, an alkyl, alkyloxyalkyl, aryl, aryloxyalkyl or aryloxyaryl group;
G is an ester, ether, carbamate, thiocarbamate, sulfone, amide, urea, thiourea, amine, sulfonamide, imine, carbonyl, or (CH$_2$)$_t$—O—;
R$^3$ and R$^4$ are each independently an alkyl, aryl, arylalkyl, heteroaryl, or an heteroarylalkyl group or optionally, R$^3$ and R$^4$ can be tethered together via (—CH$_2$—)$_q$, (—CH$_2$—)$_r$C=O(—CH$_2$—)$_s$, (—CH$_2$—)$_r$S(—CH$_2$—)$_s$, (—CH$_2$—)$_r$S=O(—CH$_2$—)$_s$ or (—CH$_2$—)$_r$S(O)$_2$(—CH$_2$—)$_s$, (—CH$_2$—)$_r$NR(—CH$_2$—)$_s$;
R$^{10}$ is a hydrogen atom or an alkyl, aryl or arylalkyl group;
R$^6$ and R$^7$ are each independently a hydrogen atom, an alkyl, aryl, arylalkyl, heteroaryl or heteroarylalkyl group;
R$^8$ and R$^9$ are each independently a hydrogen atom, an alkyl, aryl, or arylalkyl group;
R is a hydrogen atom, an alkyl or an aryl group;
q is an integer from 1 to about 7;
r is an integer from 0 to about 3;
s is an integer from 0 to about 3;
m is an integer from 2 to about 10;
t is an integer from 1 to about 10;
x is an integer from 1 to about 500; and
a polymerizable monomer.

55. A composition of formula:

L-(T-C(R$^1$)(XP)CHR$^2$GR$^3$C(=O)R$^4$)$_m$ wherein L is a linking group comprising a formula according to structure(I):

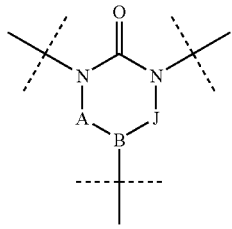
(I)

A, B, and J form a ring wherein A and J are C=O;
B is NR$^{11}$;
R$^{11}$ is a hydrogen atom, an alkyl group, an aryl group or denotes a bond with T; T is (—CH$_2$—)$_x$, (—CH$_2$CH$_2$—O—)$_x$, (—CH$_2$CH$_2$CH$_2$—O—)$_x$, (—CH$_2$CH$_2$CH$_2$CH$_2$—O—)$_4$, or forms a bond;
R$^1$ is a hydrogen atom, an alkyl, alkyloxyalkyl, aryl, aryloxyalkyl or aryloxyaryl group;
X is O, S, or NR$^8$R$^9$;
P is a hydrogen atom or a protecting group, with the provisio that P is absent when X is NR$^8$R$^9$;
R$^2$ is a hydrogen atom, an alkyl, alkyloxyalkyl, aryl, arylylalkyl or aryloxyaryl group;
G is an ester, ether, carbamate, thiocarbamate, sulfone, amide, urea, thiourea, amine, sulfonamide, imine, carbonyl, or (CH$_2$)$_r$—O—;
R$^3$ and R$^4$ are each independently an alkyl, aryl, arylalkyl, heteroaryl, or an heteroarylalkyl group, or optionally, R$^3$ and R$^4$ can be tethered together via (—CH$_2$—)$_q$, (—CH$_2$—)$_r$C=O(—CH$_2$—)$_s$, (—CH$_2$—)$_r$S(—CH$_2$—)$_s$, (—CH$_2$—)$_r$S=O(—CH$_2$—)$_s$ or (—CH$_2$—)$_r$S(O)$_2$(—CH$_2$—)$_s$, (—CH$_2$—)$_r$NR(—CH$_2$—)$_s$;
R$^{10}$ is a hydrogen atom or an alkyl, aryl or arylalkyl group;
R$^8$ and R$^9$ are each independently a hydrogen atom, an alkyl, aryl, or arylalkyl group;
R is a hydrogen atom, an alkyl or aryl group;
q is an integer from 1 to about 7;
r is an integer from 0 to about 3;
s is an integer from 0 to about 3;
m is an integer from 2 to about 10;
t is an integer from 1 to about 10; and
x is an integer from 1 to about 500; and
a polymerizable monomer.

56. A composition of formula:

L-(GTZR$^3$C(=O)R$^4$)$_m$ wherein L is a linking group comprising a formula according to structure (I):

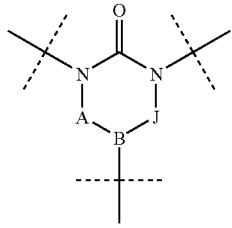
(I)

A, B, and J form a ring wherein A and J are C=O;
B is NR$^{11}$;
R$^{11}$ is a hydrogen atom, an alkyl group, an aryl group or denotes a bond;
T is (—CH$_2$—)$_x$, (—CH$_2$CH$_2$—O—)$_x$, (—CH$_2$CH$_2$CH$_2$—O—)$_x$, (—CH$_2$CH$_2$CH$_2$CH$_2$—O—)$_x$ or forms a bond;
G an ester, ether, carbamate, thiocarbamate, sulfone, amide, urea, thiourea, amine, sulfonamide, imine, carbonyl, or (CH$_2$)$_t$—O—;
Z is C=O, COO, or CONH when T is (—CH$_2$—)$_x$;
R$^3$ and R$^4$ are each independently an alkyl, aryl, arylalkyl, heteroaryl, or an heteroarylalkyl group, or optionally, R$^3$ and R$^4$ can be tethered together via (—CH$_2$—)$_q$, (—CH$_2$—)$_r$C=O(—CH$_2$—)$_s$, (—CH$_2$—)$_r$S(—CH$_2$—)$_s$, (—CH$_2$—)$_s$, (—CH$_2$—)$_r$S=O(—CH$_2$—)$_s$ or (—CH$_2$—)$_r$S(O)$_2$(—CH$_2$—)$_s$, (—CH$_2$—)$_r$NR(—CH$_2$—)$_s$;
R is a hydrogen atom or an alkyl or aryl group;
q is an integer from 1 to about 7;
r is an integer from 0 to about 3;
s is an integer from 0 to about 3;
m is an integer from 2 to about 10;
t is an integer from 1 to about 10;
x is an integer from 1 to about 500; and
a polymerizable monomer.

57. A composition of formula:

L-(TGQR$^3$C(=O)R$^4$)$_m$ wherein L is a linking group comprising a formula according to structure (I):

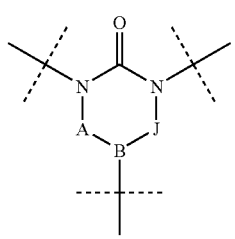
(I)

A, B, and J form a ring wherein A and J are C=O;
B is NR$^{11}$;
R$^{11}$ is a hydrogen atom, an alkyl group, an aryl group or denotes a bond;
T is (—CH$_2$—)$_x$, (—CH$_2$CH$_2$—O—)$_x$, (—CH$_2$CH$_2$CH$_2$—O—)$_x$, (—CH$_2$CH$_2$CH$_2$CH$_2$—O—)$_x$ or forms a bond;
G is an ester, ether, carbamate, thiocarbamate, sulfone, amide, urea, thiourea, amine, sulfonamide, imine, carbonyl, or (CH$_2$)$_t$—O—;
Q is (—CH$_2$—)$_p$, (—CH$_2$CH$_2$—O—)$_p$, (—CH$_2$CH$_2$CH$_2$—O—)$_p$ or (—CH$_2$CH$_2$CH$_2$CH$_2$—O—)$_p$;
R$^3$ and R$^4$ are each independently an alkyl, aryl, arylalkyl, heteroaryl, or an heteroarylalkyl group, or optionally, R$^3$ and R$^4$ can be tethered together via (—CH$_2$—)$_q$, (—CH$_2$—)$_r$C=O(—CH$_2$—)$_s$, (—CH$_2$—)$_r$S(—CH$_2$—)$_s$, (—CH$_2$—)$_r$S=O(—CH$_2$—)$_s$ or (—CH$_2$—)$_r$S(O)$_2$(—CH$_2$—)$_s$, (—CH$_2$—)$_r$NR(—CH$_2$—)$_s$;
R$^{10}$ is a hydrogen atom or an alkyl, aryl, or an arylalkyl group;
R is a hydrogen atom or an alkyl or aryl group;
q is an integer from 1 to about 7;
r is an integer from 0 to about 3;
s is an integer from 0 to about 3;
m is an integer from 2 to about 10;
p is an integer from 1 to about 10;
t is an integer from 1 to about 10; and
x is an integer from 1 to about 500; and
a polymerizable monomer.

58. A composition of formula:

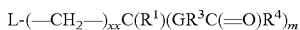

wherein L is a linking group comprising a formula according to structure (I):

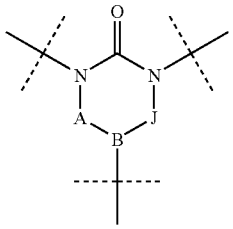

A, B, and J form a ring wherein A and J are C=O;
B is $NR^{11}$;
$R^{11}$ is a hydrogen atom, an alkyl group, an aryl group or denotes a bond;
$R^1$ is a hydrogen atom, an alkyl, alkyloxyalkyl, aryl, aryloxyalky, or aryloxyaryl group;
each G is an ester, ether, carbamate, thiocarbamate, sulfone, amide, urea, thiourea, amine, sulfonamide, imine, carbonyl, or $(CH_2)_t$—O—;
each $R^3$ and $R^4$ are each independently an alkyl, aryl, arylalkyl, heteroaryl, or an heteroarylalkyl group, or optionally, $R^3$ and $R^4$ can be tethered together via (—CH$_2$—)$_q$, (—CH$_2$—)$_r$C=O(—CH$_2$—)$_s$, (—CH$_2$—)$_r$S(—CH$_2$—)$_s$, (—CH$_2$—)$_r$S=O(—CH$_2$—)$_s$ or (—CH$_2$—)$_r$S(O)$_2$(—CH$_2$—)$_s$, (—CH$_2$—)$_r$NR(—CH$_2$—)$_s$;
each $R^{10}$ is a hydrogen atom or an alkyl, aryl, or an arylalkyl group;
each R is a hydrogen atom or an alkyl or aryl group;
each q is an integer from 1 to about 7;
each r is an integer from 0 to about 3;
each s is an integer from 0 to about 3;
m is an integer from 2 to about 10;
each t is an integer from 1 to about 10;
xx is an integer from 1 to about 10; and
a polymerizable monomer.

59. The composition of paragraph 58, wherein xx is 1, each G is (—CH$_2$)$_t$O— and t is 1, each $R^1$ is H and each $R^3$ and $R^4$ are each individually aryl groups.

60. A composition of formula:

wherein L is a linking group comprising a formula according to structure (I):

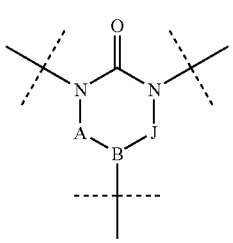

A, B, and J form a ring wherein A and J are C=O;
B is $NR^{11}$;
$R^{11}$ is a hydrogen atom, an alkyl group, an aryl group or denotes a bond;
$R^1$ is a hydrogen atom, an alkyl, alkyloxyalkyl, aryl, aryloxyalkyl or aryloxyaryl group;

X is O, S, or $NR^8R^9$;
P is a hydrogen atom or a protecting group, with the provisio that P is absent when X is $NR^8R^9$;
$R^2$ is a hydrogen atom, an alkyl, alkyloxyalkyl, aryl, aryloxyalkyl or aryloxyaryl group;
G is an ester, ether, carbamate, thiocarbamate, sulfone, amide, urea, thiourea, amine, sulfonamide, imine, carbonyl, or $(CH_2)_t$—O—;
$R^3$ and $R^4$ are each independently an alkyl, aryl, arylalkyl, heteroaryl, or an heteroarylalkyl group, or optionally, $R^3$ and $R^4$ can be tethered together via (—CH$_2$—)$_q$, (—CH$_2$—)$_r$C=O(—CH$_2$—)$_s$, (—CH$_2$—)$_r$S(—CH$_2$—)$_s$, (—CH$_2$—)$_r$S=O(—CH$_2$—)$_s$ or (—CH$_2$—)$_r$S(O)$_2$(—CH$_2$—)$_s$, (—CH$_2$—)$_r$NR(—CH$_2$—)$_s$;
$R^8$ and $R^9$ are each independently a hydrogen atom, an alkyl, aryl, or arylalkyl group;
$R^{10}$ is a hydrogen atom or an alkyl, aryl, or an arylalkyl group;
R is a hydrogen atom, an alkyl or an aryl group;
q is an integer from 1 to about 7;
r is an integer from 0 to about 3;
s is an integer from 0 to about 3;
m is an integer from 2 to about 10;
t is an integer from 1 to about 10; and
a polymerizable monomer.

61. A composition of formula:

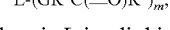

wherein L is a linking group comprising a formula according to structure (I):

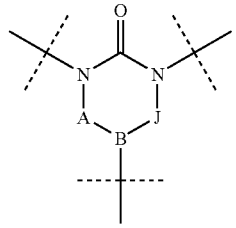

A, B, and J form a ring wherein A and J are C=O;
B is $NR^{11}$;
$R^{11}$ is a hydrogen atom, an alkyl group, an aryl group or denotes a bond;
G is an ester, ether, carbamate, thiocarbamate, sulfone, amide, urea, thiourea, amine, sulfonamide, imine, carbonyl, or $(CH_2)_t$—O—;
$R^3$ and $R^4$ are each independently an alkyl, aryl, arylalkyl, heteroaryl, or an heteroarylalkyl group, or optionally, $R^3$ and $R^4$ can be tethered together via (—CH$_2$—)$_q$, (—CH$_2$—)$_r$C=O(—CH$_2$—)$_s$, (—CH$_2$—)$_r$S(—CH$_2$—)$_s$, (—CH$_2$—)$_r$S=O(—CH$_2$—)$_s$ or (—CH$_2$—)$_r$S(O)$_2$(—CH$_2$—)$_s$, (—CH$_2$—)$_r$NR(—CH$_2$—)$_s$;
R is a hydrogen atom, an alkyl or an aryl group;
q is an integer from 1 to about 7;
r is an integer from 0 to about 3;
s is an integer from 0 to about 3;
m is an integer from 2 to about 10;
t is an integer from 1 to about 10; and
a polymerizable monomer.

62. A composition of formula:

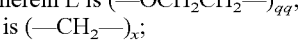

wherein L is (—OCH$_2$CH$_2$—)$_{qq}$;
T is (—CH$_2$—)$_x$;
$R^1$ is a hydrogen atom, an alkyl, alkyloxyalkyl, aryl, aryloxyalkyl or aryloxyaryl group;

X is O, S, or $NR^8R^9$;

P is a hydrogen atom or a protecting group, with the proviso that P is absent when X is $NR^8R^9$;

$R^2$ is a hydrogen atom, an alkyl, alkyloxyalkyl, aryl, aryloxylalkyl or aryloxyaryl group;

G is an ester, ether, carbamate, thiocarbamate, sulfone, amide, urea, thiourea, amine, sulfonamide, imine, carbonyl, or $(CH_2)_t$—O—;

$R^3$ and $R^4$ are each independently an alkyl, aryl, arylalkyl, heteroaryl, or an heteroarylalkyl group, or optionally, $R^3$ and $R^4$ can be tethered together via $(—CH_2—)_q$, $(—CH_2—)_r C=O(—CH_2—)_s$, $(—CH_2—)_rS(—CH_2—)_s$, $(—CH_2—)_r S=O(—CH_2—)_s$ or $(—CH_2—)_rS(O)_2(—CH_2—)_s$, $(—CH_2—)_rNR(—CH_2—)_s$;

$R^{10}$ is a hydrogen atom or an alkyl, aryl or arylalkyl group;

$R^8$ and $R^9$ are each independently a hydrogen atom, an alkyl, aryl, or arylalkyl group;

R is a hydrogen atom, an alkyl or aryl group;

q is an integer from 1 to about 7;

r is an integer from 0 to about 3;

s is an integer from 0 to about 3;

m is an integer from 2 to about 10;

t is an integer from 1 to about 10;

x is an integer from 1 to about 500;

qq is an integer from 1 to about 500; and a polymerizable monomer.

63. The composition of paragraph 62, wherein $R^1$ is H, X is O, P is H, $R^2$ is H, G is O, $R^3$ and $R^4$ are aryl groups, m is 2, x is an integer from 1 to 10 and qq is an integer from 1 to about 10.

64. A method to modify a substrate comprising the step of applying a composition of formula:

wherein L is a linking group comprising a formula according to structure (I):

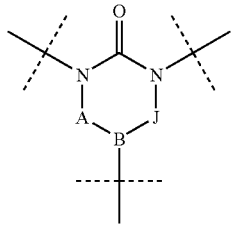

(I)

A, B, and J form a ring wherein A and J are C=O;

B is $NR^{11}$;

$R^{11}$ is a hydrogen atom, an alkyl group, an aryl group or denotes a bond;

D is $CR^6R^7$;

T is $(—CH_2—)_x$, $(—CH_2CH_2—O—)_x$, $(—CH_2CH_2CH_2—O—)_x$, $(—CH_2CH_2CH_2CH_2—O—)_x$ or forms a bond;

$R^1$ is a hydrogen atom, an alkyl, alkyloxyalkyl, aryl, aryloxylalkyl or aryloxyaryl group;

X is O, S, or $NR^8R^9$;

P is a hydrogen atom or a protecting group, with the proviso that P is absent when X is $NR^8R^9$;

$R^2$ is a hydrogen atom, an alkyl, alkyloxyalkyl, aryl, aryloxylalkyl or aryloxyaryl group;

G is an ester, ether, carbamate, thiocarbamate, sulfone, amide, urea, thiourea, amine, sulfonamide, imine, carbonyl, or $(CH_2)_t$—O—;

$R^3$ and $R^4$ are each independently an alkyl, aryl, arylalkyl, heteroaryl, or an heteroarylalkyl group or optionally, $R^3$ and $R^4$ can be tethered together via $(—CH_2—)_q$, $(—CH_2—)_r C=O(—CH_2—)_s$, $(—CH_2—)_rS(—CH_2—)_s$, $(—CH_2—)_r S=O(—CH_2—)_s$ or $(—CH_2—)_rS(O)_2(—CH_2—)_s$, $(—CH_2—)_rNR(—CH_2—)_s$;

$R^{10}$ is a hydrogen atom or an alkyl, aryl or arylalkyl group;

$R^6$ and $R^7$ are each independently a hydrogen atom, an alkyl, aryl, arylalkyl, heteroaryl or heteroarylalkyl group;

$R^8$ and $R^9$ are each independently a hydrogen atom, an alkyl, aryl, or arylalkyl group;

R is a hydrogen atom, an alkyl or an aryl group;

q is an integer from 1 to about 7;

r is an integer from 0 to about 3;

s is an integer from 0 to about 3;

m is an integer from 2 to about 10;

t is an integer from 1 to about 10;

x is an integer from 1 to about 500; and a polymerizable monomer to the surface of the substrate, such that the substrate surface is modified.

65. The method of paragraph 64, wherein the composition is photoactivated such that at least one photoactivatable group within the composition forms a bond with the surface of the substrate.

66. A method to modify a substrate comprising the step of applying a composition of formula:

wherein L is a linking group comprising a formula according to structure (I):

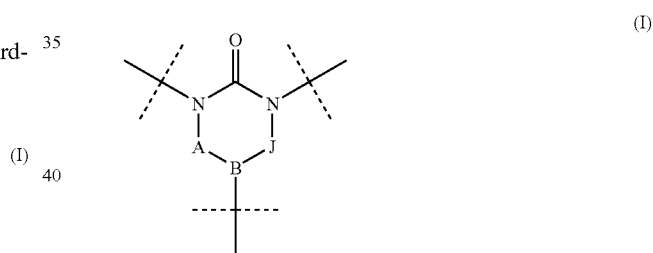

(I)

A, B, and J form a ring wherein A and J are C=O;

B is $NR^{11}$;

$R^{11}$ is a hydrogen atom, an alkyl group, an aryl group or denotes a bond with T;

T is $(—CH_2—)_x$, $(—CH_2CH_2—O—)_x$, $(—CH_2CH_2CH_2—O—)_x$, $(—CH_2CH_2CH_2CH_2—O—)$, or forms a bond;

$R^1$ is a hydrogen atom, an alkyl, alkyloxyalkyl, aryl, aryloxylalkyl or aryloxyaryl group;

X is O, S, or $NR^8R^9$;

P is a hydrogen atom or a protecting group, with the proviso that P is absent when X is $NR^8R^9$;

$R^2$ is a hydrogen atom, an alkyl, alkyloxyalkyl, aryl, aryloxylalkyl or aryloxyaryl group;

G is an ester, ether, carbamate, thiocarbamate, sulfone, amide, urea, thiourea, amine, sulfonamide, imine, carbonyl, or $(CH_2)_t$—O—;

$R^3$ and $R^4$ are each independently an alkyl, aryl, arylalkyl, heteroaryl, or an heteroarylalkyl group, or optionally, $R^3$ and $R^4$ can be tethered together via $(—CH_2—)_q$, $(—CH_2—)_r C=O(—CH_2—)_s$, $(—CH_2—)_rS(—CH_2—)_s$, $(—CH_2—)_r S=O(—CH_2—)$, or $(—CH_2—)_rS(O)_2(—CH_2—)_s$, $(—CH_2—)_rNR(—CH_2—)_s$;

$R^{10}$ is a hydrogen atom or an alkyl, aryl or arylalkyl group;

$R^8$ and $R^9$ are each independently a hydrogen atom, an alkyl, aryl, or arylalkyl group;

R is a hydrogen atom, an alkyl or aryl group;

q is an integer from 1 to about 7;

r is an integer from 0 to about 3;

s is an integer from 0 to about 3;

m is an integer from 2 to about 10;

t is an integer from 1 to about 10;

x is an integer from 1 to about 500; and a polymerizable monomer to the surface of the substrate, such that the substrate surface is modified.

67. The method of paragraph 66, wherein the composition is photoactivated such that at least one photoactivatable group within the composition forms a bond with the surface of the substrate.

68. A method to modify a substrate comprising the step of applying a composition of formula:

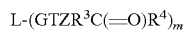
L-(GTZR$^3$C(=O)R$^4$)$_m$ wherein L is a linking group comprising a formula according to structure (I):

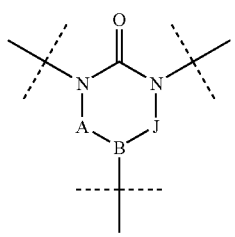
(I)

A, B, and J form a ring wherein A and J are C=O;

B is NR$^{11}$;

$R^{11}$ is a hydrogen atom, an alkyl group, an aryl group or denotes a bond;

T is (—CH$_2$—)$_x$, (—CH$_2$CH$_2$—O—)$_x$, (—CH$_2$CH$_2$CH$_2$—O—)$_x$, (—CH$_2$CH$_2$CH$_2$CH$_2$—O—)$_x$, or forms a bond;

G is an ester, ether, carbamate, thiocarbamate, sulfone, amide, urea, thiourea, amine, sulfonamide, imine, carbonyl, or (CH$_2$)$_t$—O—;

Z is C=O, COO, or CONH when T is (—CH$_2$—)$_x$;

$R^3$ and $R^4$ are each independently an alkyl, aryl, arylalkyl, heteroaryl, or an heteroarylalkyl group, or optionally, $R^3$ and $R^4$ can be tethered together via (—CH$_2$—)$_q$, (—CH$_2$—)$_r$C=O(—CH$_2$—)$_s$, (—CH$_2$—)$_r$S(—CH$_2$—)$_s$, (—CH$_2$—)$_r$S=O(—CH$_2$—)$_s$ or (—CH$_2$—)$_r$S(O)$_2$(—CH$_2$—)$_s$, (—CH$_2$—)$_r$NR(—CH$_2$—)$_s$;

R is a hydrogen atom or an alkyl or aryl group;

q is an integer from 1 to about 7;

r is an integer from 0 to about 3;

s is an integer from 0 to about 3;

m is an integer from 2 to about 10;

t is an integer from 1 to about 10;

x is an integer from 1 to about 500; and a polymerizable monomer to the surface of the substrate, such that the substrate surface is modified.

69. The method of paragraph 68, wherein the composition is photoactivated such that at least one photoactivatable group within the composition forms a bond with the surface of the substrate.

70. A method to modify a substrate comprising the step of applying a composition of formula:

L-(TGQR$^3$C(=O)R$^4$)$_m$ wherein L is a comprising a formula according to structure (I):

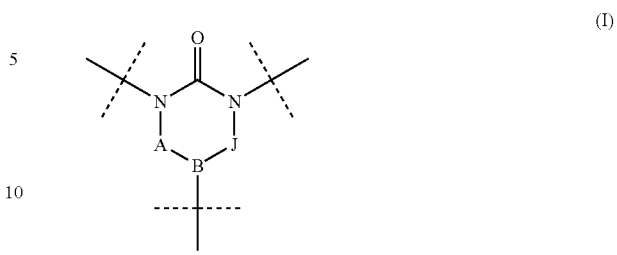
(I)

A, B, and J form a ring wherein A and J are C=O;

B is NR$^{11}$;

$R^{11}$ is a hydrogen atom, an alkyl group, an aryl group or denotes a bond with T;

T is (—CH$_2$—)$_x$, (—CH$_2$CH$_2$—O—)$_x$, (—CH$_2$CH$_2$CH$_2$—O—)$_x$, (—CH$_2$CH$_2$CH$_2$CH$_2$—O—)$_x$ or forms a bond;

G is an ester, ether, carbamate, thiocarbamate, sulfone, amide, urea, thiourea, amine, sulfonamide, imine, carbonyl, or (CH$_2$)$_t$—O—;

Q is (—CH$_2$—)$_p$, (—CH$_2$CH$_2$—O—)$_p$, (—CH$_2$CH$_2$CH$_2$—O—)$_p$ or (—CH$_2$CH$_2$CH$_2$CH$_2$—O—)$_p$;

$R^3$ and $R^4$ are each independently an alkyl, aryl, arylalkyl, heteroaryl, or an heteroarylalkyl group, or optionally, $R^3$ and $R^4$ can be tethered together via (—CH$_2$—)$_q$, (—CH$_2$—)$_r$C=O(—CH$_2$—)$_s$, (—CH$_2$—)$_r$S(—CH$_2$—)$_s$, (—CH$_2$—)$_r$S=O(—CH$_2$—)$_s$ or (—CH$_2$—)$_r$S(O)$_2$(—CH$_2$—)$_s$, (—CH$_2$—)$_r$NR(—CH$_2$—)$_s$;

$R^{10}$ is a hydrogen atom or an alkyl, aryl, or an arylalkyl group;

R is a hydrogen atom or an alkyl or aryl group;

q is an integer from 1 to about 7;

r is an integer from 0 to about 3;

s is an integer from 0 to about 3;

m is an integer from 2 to about 10;

p is an integer from 1 to about 10;

t is an integer from 1 to about 10;

x is an integer from 1 to about 500;

a polymerizable monomer to the surface of the substrate, such that the substrate surface is modified.

71. The method of paragraph 70, wherein the composition is photoactivated such that at least one photoactivatable group within the composition forms a bond with the surface of the substrate.

72. A method to modify a substrate comprising the step of applying a composition of formula:

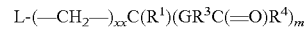
L-(—CH$_2$—)$_{xx}$C(R$^1$)(GR$^3$C(=O)R$^4$)$_m$ wherein L is a linking group comprising a formula according to structure (I):

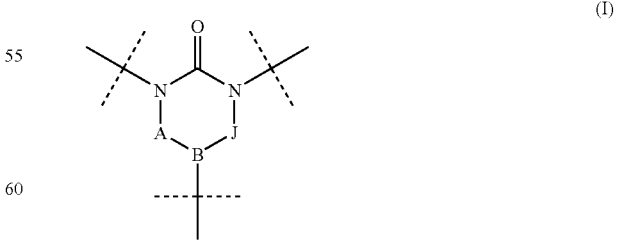
(I)

A, B, and J form in a ring wherein A and J are C=O;

B is NR$^{11}$;

$R^{11}$ is a hydrogen atom, an alkyl group, an aryl group or denotes a bond;

R[1] is a hydrogen atom, an alkyl, alkyloxyalkyl, aryl, aryloxyalky, or aryloxyaryl group;

each G is an ester, ether, carbamate, thiocarbamate, sulfone, amide, urea, thiourea, amine, sulfonamide, imine, carbonyl, or $(-CH_2)_t-O-$;

each R[3] and R[4] are each independently an alkyl, aryl, arylalkyl, heteroaryl, or an heteroarylalkyl group, or optionally, R[3] and R[4] can be tethered together via $(-CH_2-)_q$, $(-CH_2-)_rC=O(-CH_2-)_s$, $(-CH_2-)_rS(-CH_2-)_s$, $(-CH_2-)_rS=O(-CH_2-)_s$ or $(-CH_2-)_rS(O)_2(-CH_2-)_s$, $(-CH_2-)_rNR(-CH_2-)_s$;

each R[11] is a hydrogen atom or an alkyl, aryl, or an arylalkyl group;

each R is a hydrogen atom or an alkyl or aryl group;

each q is an integer from 1 to about 7;

each r is an integer from 0 to about 3;

each s is an integer from 0 to about 3;

m is an integer from 2 to about 10;

each t is an integer from 1 to about 10;

xx is an integer from 1 to about 10; and a polymerizable monomer to the surface of the substrate, such that the substrate surface is modified.

73. The method of paragraph 72, wherein the composition is photoactivated such that at least one photoactivatable group within the composition forms a bond with the surface of the substrate.

74. A method to modify a substrate comprising the step of applying a composition of formula:

L-(—C(R[1])(XP)CHR[2]GR[3]C(=O)R[4])_m wherein L is a linking group comprising a formula according to structure (I):

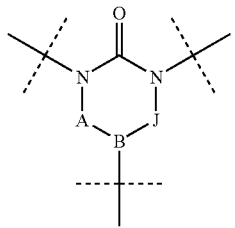

(I)

A, B, and J form a ring wherein A and J are C=O;

B is NR[11];

R[11] is a hydrogen atom, an alkyl group, an aryl group or denotes a bond;

R[1] is a hydrogen atom, an alkyl, alkyloxyalkyl, aryl, aryloxyalkyl or aryloxyaryl group;

X is O, S, or NR[8]R[9];

P is a hydrogen atom or a protecting group, with the provisio that P is absent when X is NR[8]R[9];

R[2] is a hydrogen atom, an alkyl, alkyloxyalkyl, aryl, aryloxyalkyl or aryloxyaryl group;

G is an ester, ether, carbamate, thiocarbamate, sulfone, amide, urea, thiourea, amine, sulfonamide, imine, carbonyl, or $(-CH_2)_t-O-$;

R[3] and R[4] are each independently an alkyl, aryl, arylalkyl, heteroaryl, or an heteroarylalkyl group, or optionally, R[3] and R[4] can be tethered together via $(-CH_2-)_q$, $(-CH_2-)_rC=O(-CH_2-)_s$, $(-CH_2-)_rS(-CH_2-)_s$, $(-CH_2-)_rS=O(-CH_2-)_s$ or $(-CH_2-)_rS(O)_2(-CH_2-)_s$, $(-CH_2-)_rNR(-CH_2-)_s$;

R[8] and R[9] are each independently a hydrogen atom, an alkyl, aryl, or arylalkyl group;

R[10] is a hydrogen atom or an alkyl, aryl, or an arylalkyl group;

R is a hydrogen atom, an alkyl or an aryl group;

q is an integer from 1 to about 7;

r is an integer from 0 to about 3;

s is an integer from 0 to about 3;

m is an integer from 2 to about 10;

t is an integer from 1 to about 10; and a polymerizable monomer to the surface of the substrate, such that the substrate surface is modified.

75. The method of paragraph 74, wherein the composition is photoactivated such that at least one photoactivatable group within the composition forms a bond with the surface of the substrate.

76. A method to modify a substrate comprising the step of applying a composition of formula:

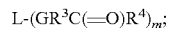

L-(GR[3]C(=O)R[4])_m;

wherein L is a linking group comprising a formula according to structure (I):

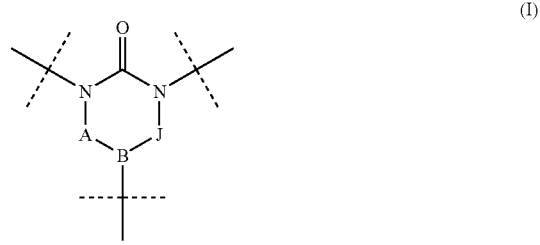

(I)

A, B, and J form a ring wherein A and J are C=O;

B is NR[11];

R[11] is a hydrogen atom, an alkyl group, an aryl group or denotes a bond;

G is an ester, ether, carbamate, thiocarbamate, sulfone, amide, urea, thiourea, amine, sulfonamide, imine, carbonyl, or $(-CH_2)_t-O-$;

R[3] and R[4] are each independently an alkyl, aryl, arylalkyl, heteroaryl, or an heteroarylalkyl group, or optionally, R[3] and R[4] can be tethered together via $(-CH_2-)_q$, $(-CH_2-)_r$C=O $(-CH_2-)_s$, $(-CH_2-)_rS(-CH_2-)_s$, $(-CH_2-)_r$ S=O$(-CH_2-)_s$ or $(-CH_2-)_rS(O)_2(-CH_2-)_s$, $(-CH_2-)_rNR(-CH_2-)_s$;

R is a hydrogen atom, an alkyl or an aryl group;

q is an integer from 1 to about 7;

r is an integer from 0 to about 3;

s is an integer from 0 to about 3;

m is an integer from 2 to about 10;

t is an integer from 1 to about 10; and a polymerizable monomer to the surface of the substrate, such that the substrate surface is modified.

77. The method of paragraph 76, wherein the composition is photoactivated such that at least one photoactivatable group within the composition forms a bond with the surface of the substrate.

78. A method to modify a substrate comprising the step of applying a composition of formula:

L-(T-C(R[1])(XP)CHR[2]GR[3]C(=O)R[4])_m wherein L is $(-OCH_2CH_2)_{qq}$;

T is $(-CH_2-)_x$;

R[1] is a hydrogen atom, an alkyl, alkyloxyalkyl, aryl, aryloxyalkyl or aryloxyaryl group;

X is O, S, or NR[8]R[9];

P is a hydrogen atom or a protecting group, with the provisio that P is absent when X is NR[8]R[9];

$R^2$ is a hydrogen atom, an alkyl, alkyloxyalkyl, aryl, aryloxylalkyl or aryloxyaryl group;

G is an ester, ether, carbamate, thiocarbamate, sulfone, amide, urea, thiourea, amine, sulfonamide, imine, carbonyl, or $(CH_2)_t$—O—;

$R^3$ and $R^4$ are each independently an alkyl, aryl, arylalkyl, heteroaryl, or an heteroarylalkyl group, or optionally, $R^3$ and $R^4$ can be tethered together via $(-CH_2-)_q$, $(-CH_2-)_r$C=O$(-CH_2-)_s$, $(-CH_2-)_rS(-CH_2-)_s$, $(-CH_2-)_r$S=O$(-CH_2-)_s$ or $(-CH_2-)_rS(O)_2(-CH_2-)_s$, $(-CH_2-)_r NR(-CH_2-)_s$;

$R^{10}$ is a hydrogen atom or an alkyl, aryl or arylalkyl group;

$R^8$ and $R^9$ are each independently a hydrogen atom, an alkyl, aryl, or arylalkyl group;

R is a hydrogen atom, an alkyl or aryl group;

q is an integer from 1 to about 7;

r is an integer from 0 to about 3;

s is an integer from 0 to about 3;

m is an integer from 2 to about 10;

t is an integer from 1 to about 10;

x is an integer from 1 to about 500;

qq is an integer from 1 to about 500; and a polymerizable monomer to the surface of the substrate, such that the substrate surface is modified.

79. The method of paragraph 78, wherein the composition is photoactivated such that at least one photoactivatable group within the composition forms a bond with the surface of the substrate.

80. A polymeric brush composition or coating comprising the reaction product of any of paragraphs 1 through 22, 39 through 42, 47 through 49 or 54 through 63.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight.

Example 1

Synthesis of Trifunctional Triazine Crosslinker 1.2 g (4 mmol) of triglycidyl isocyanurate (Aldrich Chemicals, Milwaukee, Wis.) and 2.4 g (12 mmol) of 4-hydroxybenzophenone (Aldrich Chemicals, Milwaukee, Wis.) were mixed in a 50-ml round bottom flask containing a magnetic stir bar. The flask was flushed with argon for 10 min and heated to 130° C. in an oil bath. Once the reaction mixture melted, 6 mg (0.02 mmol) of triphenylphosphine (Aldrich Chemicals, Milwaukee, Wis.) was added. The mixture was stirred for another 2 minutes under argon and cooled to room temperature. The reaction residue was dissolved in 30 ml chloroform, then washed with 4N NaOH (30 ml×3) and deionized water (30 ml×3). The organic layer was dried over magnesium sulfate and concentrated to dryness on the under reduced pressure. The product was purified by column chromatography (silica gel, 230-400 mesh, Whatman, Inc.) using ethyl acetate as eluent ($R_f$~4.5). The fractions containing the pure product were combined and concentrated under reduced pressure and a white powder was obtained after drying under vacuum (yield 70%).

The crosslinker is soluble in most common solvents including chloroform, methylene chloride, acetone, ethyl acetate, isopropanol, etc. $^1$H NMR (CDCl$_3$) confirmed the structure of the product. The peaks at d 7.78 ppm (m, 12H), 7.46 ppm (m, 9H), 6.98 ppm (m, 6H) were the typical signals from 4-substituted benzophenone. The peak at d 4.35 ppm (m, 6H) was assigned to the protons of methylene connected to phenoxy group. The peak at d 4.13 ppm (m, 9H) was a combination of 6 protons of 3 methylene groups connected to nitrogen atom and 3 protons from 3 methine groups. The peak at d 3.00 ppm (s, 3H) corresponded to hydroxyl groups.

Example 2

Synthesis of Photoreactive Glycol Crosslinker 2.26 g 4-hydroxybenzophenone (Aldrich Chemicals, Milwaukee, Wis.) was dissolved in 50 ml of acetone, and 0.532 ml of glycerol triglycidyl ether (Polysciences, Warrington, Pa.), and 3.3 g potassium carbonate (Aldrich Chemicals, Milwaukee, Wis.) were added to the solution. The reaction mixture was heated to reflux over 24 hours. After 24 hours of heating, thin layer chromatography (TLC) showed consumption of the glycerol starting material (eluent 20:1 Chloroform: methanol) and the emergence of three uv active spots. The acetone was removed by rotary evaporation and the residue was dissolved in chloroform, and filtered. The resulting chloroform solution was washed three times with 4N NaOH aqueous solution, once with deionized water, then twice with 1N HCl aqueous solution, and three times again with deionized water. The chloroform solution was dried over magnesium sulfate, filtered, and the solvent removed by rotary evaporation. The resulting oil was washed three times with diethyl ether and dried. This treatment removed all 4-hydroxybenzophenone starting material, with TLC revealing the same three uv active spots. These three products presumably correspond to single, double, and triple substitution of benzophenone on the glycerol compound.

Example 3

Diethylene Glycol Photocrosslinker Synthesis

4-Hydroxybenzophenone, 2.2758 g (11.4811 mMol, 2 mol eq, Alfa Aesar, Ward Hill, Mass.), was added to a 100 mL round bottom flask equipped with a reflux condenser and dissolved in 75 mL of acetone. Ethylene glycol diglycidyl ether, 1.0000 g (5.7405 mMol, 1 mol eq Aldrich Chemicals, Milwaukee, Wis.) followed by potassium carbonate, 3.1736 g (22.9621 mMol, 4 mol eq), was then added to the mixture and was heated at reflux overnight. After cooling, the remaining solid was filtered and organic layer was removed in vacuo. The crude product mixture was redissolved in 60 mL of chloroform and the residual 4-Hydroxybenzophenone was removed by washing with a 4N NaOH aqueous solution. The organic layer was then dried over MgSO$_4$ and filtered to remove drying agent. A portion of the chloroform solvent was removed in vacuo until 5 mL remained. The product was isolated by silica column (EMD Silica Gel 0.040-0.063 mm, 230-400 mesh, 60 Å) using (9:1) Ethyl Acetate:Hexane as eluent. Elution was monitored by TLC. $R_f$ value of desired product was 0.40 in same eluent. $^1$H NMR (CDCl$_3$): δ=7.7-7.9, 7.4-7.6, 6.9-7.1 (m, characteristic of benzophenone), 4.2-4.3 (m), 4.0-4.2 (m), 3.6-3.8 ppm (m).

Example 4

Synthesis of Urea Photo-Crosslinker

Bis-2,3-dihydroxypropylurea, 0.3000 g (1.4408 mMol, 1 mol equiv. Aldrich Chemicals, Milwaukee, Wis.), was added to a 50 mL round bottom flask under argon sweep and dissolved in 20 mL of DMF (Fisher Scientific, Pittsburgh, Pa.). Sodium hydride (60% dispersion in mineral oil, Aldrich Chemicals, Milwaukee, Wis.), 0.2305 g (5.7633 mMol, 4 mol eq), was then added and stirred at room temperature for 20 minutes. 4-(Bromomethyl)benzophenone, 1.5858 g (5.7633 mMol, 4 mol equiv. Aldrich Chemicals, Milwaukee, Wis.), was added to the mixture and heated at reflux under positive argon pressure for five hours. After cooling, the reaction mixture was dissolved in 200 mL of deionized water and the crude product was extracted with chloroform. The organic layer was then dried over magnesium sulfate and filtered to remove the drying agent. The chloroform was removed in vacuo and the crude product was redissolved in a minimal amount of (85:15) $CHCl_3$:MeOH. The product was isolated by silica gel column (EMD Silica Gel 0.040-0.063 mm, 230-400 mesh, 60 Å) using (85:15) $CHCl_3$:MeOH as eluent. Elution was monitored by TLC. $R_f$ value of desired product was 0.74 in the same eluent. Several spots were isolated together and may represent two, three, and four functionalized crosslinkers. $^1$H NMR ($CDCl_3$): δ=7.3-7.9 (m, characteristic benzophenone pattern), 4.5-4.7 (m), 3.5-3.8 ppm (m).

Example 5

Synthesis of Polyalcohol Photo-Crosslinker 3,4-O-Isopropylidene-D-mannitol, 0.5000 g (2.2498 mMol, 1 mol eq, Aldrich Chemicals, Milwaukee, Wis.), was added to a 50 mL round bottom flask equipped with a reflux condenser and dissolved in 25 mL of chloroform under argon sweep. NaH (with 60% dispersion in mineral oil, Aldrich Chemicals, Milwaukee, Wis.), 0.2700 g (6.7495 mMol, 3 mol eq), was added and then stirred for 30 minutes. 4-(Bromomethyl)benzophenone (Aldrich Chemicals, Milwaukee, Wis.), 0.1.23808 g (4.4996 mMol, 2 mol eq), was added to the mixture and heated at reflux overnight under positive argon pressure. After cooling, the organic layer was filtered to remove precipitate. A portion of the chloroform solvent was removed in vacuo until 5 mL remained. The product was isolated by silica gel column (EMD Silica Gel 0.040-0.063 mm, 230-400 mesh, 60 Å) using chloroform as eluent. Elution was monitored by TLC. $R_f$ value of desired product was 0.40 in the same eluent. Three compounds were isolated and may represent different isomers of the compound. $^1$H NMR ($CDCl_3$): δ=7.3-7.9 (m, characteristic of benzophenone pattern), 4.6-5.0 (dd), 4.5-4.6 (s), 3.6-3.9 (m), 1.5-1.6 ppm (s).

Example 6

Synthesis of Photo-Uracil Crosslinker

6-Aminouracil, 0.1091 g (0.8581 mMol, 1 mol eq, Aldrich Chemicals, Milwaukee, Wis.), was added to a 100 mL round bottom flask equipped with a reflux condenser and dissolved in 50 mL of chloroform under argon sweep. 4-(Benzoyl) benzoic acid chloride, 0.4199 g (1.7161 mMol, 2 mol eq, Aldrich Chemicals, Milwaukee, Wis.), 4-Dimethylaminopyridine, 0.01260 g (3-5 wt % of 4-(Benzoyl)benzoic acid chloride, Aldrich Chemicals, Milwaukee, Wis.), and Triethylamine, 0.1042 g (1.02969 mMol, 1.2 mol eq, Aldrich Chemicals, Milwaukee, Wis.) were heated at reflux under positive argon pressure overnight. After cooling, the reaction mixture was filtered to remove precipitate. The organic layer was removed in vacuo and the remaining crude reaction mixture was redissolved in a minimal amount of (9:1) $CHCl_3$:MeOH. The desired product was isolated by silica gel column (EMD Silica Gel 0.040-0.063 mm, 230-400 mesh, 60 Å) using the (9:1) $CHCl_3$:MeOH as eluent. Monitor elution by TLC. $R_f$ value of desired product was 0.56 in the same eluent.

Example 7

Synthesis of TEG Photo-Crosslinker 1.94 g of tetraethylene glycol (Aldrich Chemicals, Milwaukee, Wis.) was dried under vacuum at 50° C. for 2 h and dissolved in 50 ml anhydrous tetrahydrofuran. 6.8 g of 4-(bromomethyl)benzophenone (Aldrich Chemicals, Milwaukee, Wis.) and 1.8 g sodium hydride (60% in mineral oil, Aldrich Chemicals, Milwaukee, Wis.) were added to the solution. The mixture was stirred overnight under refluxing condition and argon protection. The reaction solution was cooled to room temperature and filtered. The filtrate was concentrated by rotary evaporation and the residue was purified on column chromatography (silica gel, 230-400 mesh, Whatman, Inc.) using 25:1 chloroform/methanol mixture as eluent. The fractions containing the pure product were combined and concentrated to dryness by rotary evaporation to yield yellowish oil (yield 80%).

The TEG crosslinker is soluble in most common solvents including chloroform, methylene chloride, tetrahydrofuran, acetone, ethyl acetate, isopropanol, etc. $^1$H NMR ($CDCl_3$) confirmed the structure of the product. The peaks at 7.49~7.79 ppm (m, 18H) were the typical signals from 4-substituted benzophenone. The peak at 4.66 ppm (s, 4H) was assigned to the protons of methylene connected to benzophenone group. The peak at 3.70 ppm (m, 16H) corresponded to ethylene groups.

Example 8

Synthesis of HEG Photo-Crosslinker 1.70 g of hexaethylene glycol (Aldrich Chemicals, Milwaukee, Wis.) was dried under vacuum at 50° C. for 2 h and dissolved in 50 ml anhydrous tetrahydrofuran. 3.7 g of 4-(bromomethyl)benzophenone (Aldrich Chemicals, Milwaukee, Wis.) and 1.5 g sodium hydride (60% in mineral oil, Aldrich Chemicals, Milwaukee, Wis.) were added to the solution. The mixture was stirred overnight under refluxing condition and argon protection. The reaction solution was cooled to room temperature and filtered. The filtrate was concentrated by rotary evaporation and the residue was purified on column chromatography (silica gel, 230-400 mesh, Whatman, Inc.) using 25:1 chloroform/methanol mixture as eluent. The fractions containing the pure product were combined and concentrated to dryness by rotary evaporation to yield yellowish oil (yield 70%).

The HEG crosslinker is very soluble in most common solvents including chloroform, methylene chloride, tetrahydrofuran, acetone, ethyl acetate, isopropanol, etc. and slightly soluble in water. $^1$H NMR ($CDCl_3$) confirmed the structure of the product. The peaks at 7.26~7.79 ppm (m, 18H) were the typical signals from 4-substituted benzophenone. The peak at 4.64 ppm (s, 4H) was assigned to the protons of methylene connected to benzophenone group. The peak at 3.66 ppm (m, 24H) corresponded to ethylene groups.

Example 9

HDPE Treated with BP and Sulfobetaine Methacrylamide

1×3 cm high density polyethylene (HDPE) (McMaster-Carr, Chicago, Ill.) coupons were immersed in an acetone solution containing 10 mg/mL benzophenone (BP) (Aldrich Chemicals, Milwaukee) for 30 s and then dried in the dark at room temperature to remove acetone. Sulfobetaine methacrylamide (SBMAM) (Aldrich Chemicals, Milwaukee) was dissolved in deionized water to obtain a concentration of 0.5 mol/L. Then the HDPE coupons coated with benzophenone were immersed in the aqueous SBMAM solution and degassed under argon. Photo-induced graft polymerization on the HDPE surface was performed with ultraviolet light (300 to 400 nm) for 1 hr (Harland Medical UVM400, Eden Prairie, Minn.). After polymerization, the HDPE-g-SBMAM coupons were removed, washed with deionized water and isopropanol, and dried at room temperature.

Example 10

HDPE Treated with Triazine Crosslinker of Example 1 and SBMAM

1×3 cm high density polyethylene (HDPE) (McMaster-Carr, Chicago, Ill.) coupons were immersed in an acetone solution containing 10 mg/mL the triazine crosslinker of Example 1 for 30 s and then dried in the dark at room temperature to remove acetone. Sulfobetaine methacrylamide (SBMAM) (Aldrich Chemicals, Milwaukee) was dissolved in deionized water to obtain a concentration of 0.5 mol/L. Then the HDPE coupons coated with the triazine crosslinker were immersed in the aqueous SBMAM solution and degassed under argon. Photo-induced graft polymerization on the HDPE surface was performed with ultraviolet light (300 to 400 nm) for 1 hr (Harland Medical UVM400, Eden Prairie, Minn.). After polymerization, the HDPE-g-SBMAM coupons were removed, washed with deionized water and isopropanol, and dried at room temperature.

Example 11

Nylon Treated with BP and SBMAM

1×3 cm Nylon (McMaster-Carr, Chicago, Ill.) coupons were immersed in an acetone solution containing 10 mg/mL benzophenone (Aldrich Chemicals, Milwaukee) for 30 s and then dried in the dark at room temperature to remove acetone. Sulfobetaine methacrylamide (SBMAM) (Aldrich Chemicals, Milwaukee) was dissolved in deionized water to obtain a concentration of 0.5 mol/L. Then the Nylon coupons coated with benzophenone were immersed in the aqueous SBMAM solution and degassed under argon. Photo-induced graft polymerization on the Nylon surface was performed with ultraviolet light (300 to 400 nm) for 1 hr (Harland Medical UVM400, Eden Prairie, Minn.). After polymerization, the Nylon-g-SBMAM coupons were removed, washed with deionized water and isopropanol, and dried at room temperature.

Example 12

Nylon Treated with Triazine Crosslinker of Example 1 and SBMAM

1×3 cm Nylon (McMaster-Carr, Chicago, Ill.) coupons were immersed in an acetone solution containing 10 mg/mL the triazine crosslinker of example 1 for 30 s and then dried in the dark at room temperature to remove acetone. Sulfobetaine methacrylamide (SBMAM) (Aldrich Chemicals, Milwaukee) was dissolved in deionized water to obtain a concentration of 0.5 mol/L. Then the Nylon coupons coated with the triazine crosslinker were immersed in the aqueous SBMAM solution and degassed under argon. Photo-induced graft polymerization on the Nylon surface was performed with ultraviolet light (300 to 400 nm) for 1 hr (Harland Medical UVM400, Eden Prairie, Minn.). After polymerization, the Nylon-g-SBMAM coupons were removed, washed with deionized water and isopropanol, and dried at room temperature.

Example 13

Preparation of CBMA

A carboxybetaine methacrylate (CBMA) monomer, 2-carboxy-N,N-dimethyl-N-(2'-methacryloyloxyethyl) ethanaminium inner salt, was synthesized by the reaction of 2-dimethylaminoethyl methacrylate (DMAEM) (Aldrich Chemicals, Milwaukee) with β-propiolactone (Aldrich Chemicals, Milwaukee). 5 mL β-Propiolactone in 10 mL of anhydrous acetone was added dropwise to a solution of 10 mL DMAEM dissolved in 300 mL of anhydrous acetone. The reaction mixture was stirred under argon protection at room temperature overnight. After removing acetone, the residue was washed with hexane twice and dried under vacuum, yielding 9.2 g CBMA product.

Example 14

HDPE Treated with BP and CBMA

1×3 cm high density polyethylene (HDPE) (McMaster-Carr, Chicago, Ill.) coupons were immersed in an acetone solution containing 10 mg/mL benzophenone (Aldrich Chemicals, Milwaukee) for 30 s and then dried in the dark at room temperature to remove acetone. CBMA was dissolved in deionized water to obtain a concentration of 0.5 mol/L. Then the HDPE coupons coated with benzophenone were immersed in the aqueous CBMA solution and degassed under argon. Photo-induced graft polymerization on the HDPE surface was performed with ultraviolet light (300 to 400 nm) for 1 hr (Harland Medical UVM400, Eden Prairie, Minn.). After polymerization, the HDPE-g-CBMA coupons were removed, washed with deionized water and isopropanol, and dried at room temperature.

Example 15

HDPE Treated with Triazine Crosslinker of Example 1 and CBMA

1×3 cm high density polyethylene (HDPE) (McMaster-Carr, Chicago, Ill.) coupons were immersed in an acetone solution containing 10 mg/mL the triazine crosslinker of Example 1 for 30 s and then dried in the dark at room temperature to remove acetone. CBMA was dissolved in deionized water to obtain a concentration of 0.5 mol/L. Then the HDPE coupons coated with the triazine crosslinker were immersed in the aqueous CBMA solution and degassed under argon. Photo-induced graft polymerization on the HDPE surface was performed with ultraviolet light (300 to 400 nm) for 1 hr (Harland Medical UVM400, Eden Prairie, Minn.). After polymerization, the HDPE-g-CBMA coupons were removed, washed with deionized water and isopropanol, and dried at room temperature.

Example 16

Nylon Treated with BP and CBMA

1×3 cm Nylon (McMaster-Carr, Chicago, Ill.) coupons were immersed in an acetone solution containing 10 mg/mL benzophenone (Aldrich Chemicals, Milwaukee) for 30 s and then dried in the dark at room temperature to remove acetone. CBMA was dissolved in deionized water to obtain a concentration of 0.5 mol/L. Then the Nylon coupons coated with benzophenone were immersed in the aqueous CBMA solution and degassed under argon. Photo-induced graft polymerization on the Nylon surface was performed with ultraviolet light (300 to 400 nm) for 1 hr (Harland Medical UVM400, Eden Prairie, Minn.). After polymerization, the Nylon-g-CBMA coupons were removed, washed with deionized water and isopropanol, and dried at room temperature.

Example 17

Nylon Treated with Triazine Crosslinker of Example 1 and CBMA

1×3 cm Nylon (McMaster-Carr, Chicago, Ill.) coupons were immersed in an acetone solution containing 10 mg/mL the triazine crosslinker of example 1 for 30 s and then dried in the dark at room temperature to remove acetone. CBMA was dissolved in deionized water to obtain a concentration of 0.5 mol/L. Then the Nylon coupons coated with the triazine crosslinker were immersed in the aqueous CBMA solution and degassed under argon. Photo-induced graft polymerization on the Nylon surface was performed with ultraviolet light (300 to 400 nm) for 1 hr (Harland Medical UVM400, Eden Prairie, Minn.). After polymerization, the Nylon-g-CBMA coupons were removed, washed with deionized water and isopropanol, and dried at room temperature.

Example 18

Contact Angles of Examples 9 through 12 and 14 through 17

The static water-contact angles of coated coupons were measured with a contact angle goniometer (400, Micro-Vu, Windsor, Calif.). Measurements were taken 5 seconds after putting 5 µL deionized water drops on the surface. 5 replicate measurements were performed on each sample, and the average values were taken as the contact angles.

| Surfaces | Water Contact Angle |
| --- | --- |
| HDPE | 85 |
| Nylon | 52 |
| HDPE-g-SBMAM (BP) | 12 |
| HDPE-g-SBMAM (Triazine crosslinker of example 1) | 6 |
| Nylon-g-SBMAM (BP) | 10 |
| Nylon-g-SBMAM (Triazine crosslinker of example 1) | 5 |
| HDPE-g-CBMA (BP) | 20 |
| HDPE-g-CBMA (Triazine crosslinker of example 1) | 18 |
| Nylon-g-CBMA (BP) | 16 |
| Nylon-g-CBMA (Triazine crosslinker of example 1) | 15 |

The contact angle results show that compared to benzophenone the graft polymerization induced by the triazine crosslinker of example 1 treated samples generate more hydrophilic surfaces.

Example 19

Microscopic Analysis of Examples 11 and 12

Nylon-g-SBMAM coupons were investigated under optical microscope. The images show that the triazine crosslinker of example 1 treated samples produce more uniform coating than benzophenone. See FIG. 1 for example.

Example 20

Nonspecific Protein Adsorption of Examples 11 and 12

Figure 2:
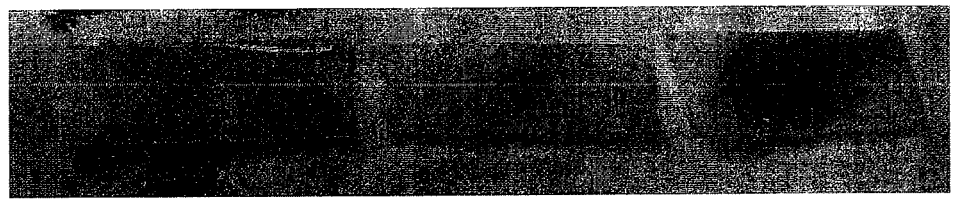
FIG. 2 demonstrates that nylon coupons treated with compositions of the invention have decreased non-specific protein adsorption as compared to an untreated nylon coupon.

Nylon-g-SBMAM coupons were investigated for nonspecific protein adsorption. Nylon-g-SBMAM (BP), Nylon-g-SBMAM (triazine crosslinker of example 1) and uncoated Nylon coupons were incubated with 300 uL monoclonal anti-rabbit IgG peroxidase conjugate (1:10,000 in PBS) (Sigma) at room temperature for 1 hr, and rinsed with PBS-Tween and PBS. Then standard peroxidase substrate was applied to the surfaces. Pictures were taken after 2 min. The results noted in FIG. 2 provides that both SBMAM coatings exhibited high resistance to nonspecific protein adsorption.

Example 21

Solution Polymerization of Examples 16 and 17

After graft polymerization in Examples 16 and 17, the Nylon-g-CBMA (BP) and Nylon-g-CBMA (triazine crosslinker of Example 1) coupons were removed and the viscosity of the monomer solutions was measured using a Brookfield Digital Viscometer (Middleboro, Mass.). The CBMA solution without graft polymerization was also measured as a control. The viscosity is 1.3 cP for CBMA solution without grafting, 9.3 cP for CBMA (triazine crosslinker of Example 1) and 41.7 cP for CBMA (BP). The results show that more solution polymerization occurred in BP induced graft polymerization than in the triazine crosslinker of Example 1 induced graft polymerization.

Example 22

Bacterial Adherence Assay of Example 10

A bacterial culture of *S. aureus* ATCC#6538 was grown overnight on TSA (tryptic soy agar, AcuMedia, Lansing Mich.). Using a sterile swab, *S. aureus* was transferred from the TSA plate to BB (Butterfield's buffer, PML Microbiologicals, Durham N.C.) to make a $10^8$ CFU/mL suspension. The $10^8$ CFU/mL suspension was then diluted in BB to make a $10^4$ CFU/mL suspension. Final cell density was calculated by plating *S. aureus* suspension to TSA.

The grafted HDPE samples, in triplicate, of Example 10 were incubated with 15 mL $10^4$ CFU/mL *S. aureus* suspension for 2 hours (25° C., shaking at 250 RPM). Coupons were removed from the bacterial suspension and placed in a fresh vial of 15 mL BB (2 minutes, 25° C., shaking at 250 RPM). Coupons were removed from the rinse vial and place in a fresh vial of 15 mL BB (total of 4 coupon rinse cycles). After the last rinse, coupons were moved to a fresh vial of 5 mL BB and sonicated (40 kHz, Bransonic 2510, Danbury Conn.) (1 minute sonication, 1 minute rest, 1 minute sonication) to remove adhered bacteria. 1 mL of the BB sonication solution was plated to TSA (pour plate method, 37° C. incubation for 18 hours). The sonication procedure was repeated to ensure the efficacy of the first sonication cycle.

The results showed that the bacterial density on the SBMAM grafted HDPE samples was 1.79±1.08 cells/mm$^2$, suggesting a significant reduction of bacterial adhesion compared to a density of 10$^3$ cells/mm$^2$ on untreated HDPE reported in the literature (http://repositorium.sdum.uminho.pt/handle/1822/6706).

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claim.

What is claimed is:

1. A composition comprising a photoreactive cross-linking compound having a formula:

wherein L is a linking group comprising a formula according to structure (I):

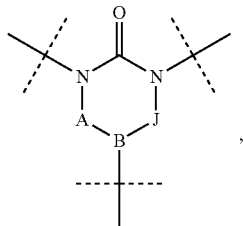

A, B, and J form a ring wherein A and J are C=O;
B is NR$^{11}$;
R$^{11}$ is a hydrogen atom, an alkyl group, an aryl group or denotes a bond with T;
T is —(CH$_2$)$_x$—;
R$^1$ is a hydrogen atom, an alkyl, alkyoxyalky, aryl, aryloxyalkyl or aryloxyaryl group;
X is O;
P is a hydrogen atom;
R$^2$ is a hydrogen atom, an alkyl, alkyloxyalkyl, aryl, aryloxyalkyl or aryloxyaryl group;
G is —O—;
R$^3$ and R$^4$ are each independently an aryl;
R is a hydrogen atom, an alkyl or aryl group;
m is 2 or 3;
x is an integer from 1 to about 500; and
a polymerizable monomer.

2. The composition of claim 1, wherein the polymerizable monomer has an acrylate, allylic, methacrylate, vinyl or diarylketone containing moiety.

3. The composition of claim 2, wherein the acrylate, allylic, methacrylate, vinyl or diarylketone polymerizable monomer further includes a zwitterionic moiety.

4. The composition of claim 3 wherein the polymerizable monomer is N,N-dimethyl-N-acryloyloxyethyl-N-(3-sulfopropyl)-ammonium betaine, N,N-dimethyl-N-methacryloyloxyethyl-N-(3-sulfopropyl)-ammonium betaine, N,N-dimethyl-N-acrylamidopropyl-N-(2-carboxymethyl)-ammonium betaine, N,N-dimethyl-N-methacrylamidopropyl-N-(2-carboxymethyl)-ammonium betaine, N,N-dimethyl-N-acrylamidopropyl-N-(3-sulfopropyl)-ammonium betaine, N,N-dimethyl-N-methacrylamidopropyl-N-(3-sulfopropyl)-ammonium betaine, N,N-dimethyl-N-acrylamidopropyl-N-(2-carboxymethyl)-ammonium betaine, N,N-dimethyl-N-methacrylamidopropyl-N-(2-carboxymethyl)-ammonium betaine, 2-(methylthio)ethyl methacryloyl-S-(sulfopropyl)-sulfonium betaine, 2-[(2-acryloylethyl)dimethylammonio] ethyl 2-methyl phosphate, 2-(acryloyloxyethyl)-2'-(trimethylammonium)ethyl phosphate, [(2-acryloylethyl) dimethylammonio]methyl phosphonic acid, 2-[(3-acrylamidopropyl)dimethylammonio]ethyl 2'-isopropyl phosphate (AAPI), 1-vinyl-3-(3-sulfopropyl)imidazolium hydroxide, (2-acryloxyethyl) carboxymethyl methylsulfonium chloride, 1-(3-sulfopropyl)-2-vinylpyridinium betaine, N-(4-sulfobutyl)-N-methyl-N,N-diallylamine ammonium betaine (MDABS),2-methacryloyloxyethyl phosphorylcholine, or N,N-diallyl-N-methyl-N-(2-sulfoethyl) ammonium betaine.

5. The composition of claim 1, further comprising a photoinitiator, wherein the initiator is benzophenone, an acetophenone derivative, a benzoin derivative, a benzilketal, a hydroxyalkylphenone, an aminoalkylphenone, an O-acyl oximoketone, an acylphosphonate, a thiobenzoic S-ester, a triazine, a 1,2 diketone, a quinone, a coumarins, a xanthone, or mixtures thereof.

6. The composition of claim 1, wherein the photoreactive cross linking compound has a formula:

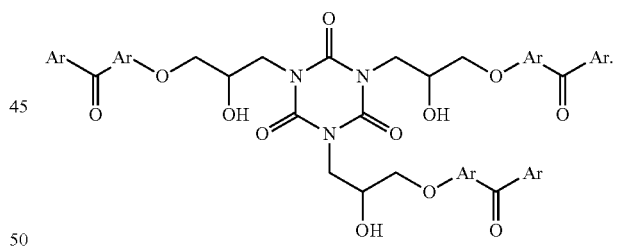

7. The composition of claim 6, wherein the structure of the photoreactive cross linking compound has a formula:

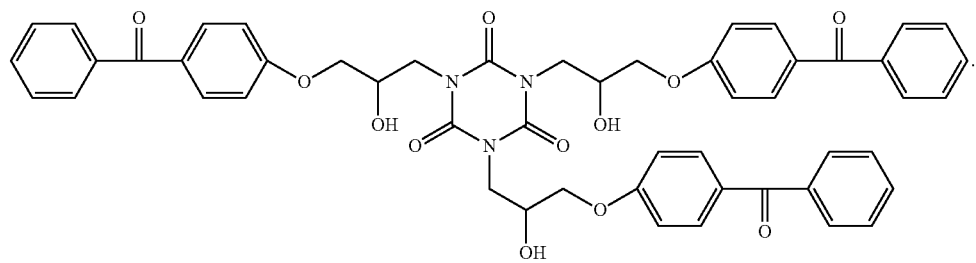 [SMILES: O=C(c1ccccc1)c1ccc(OCC(O)Cn2c(=O)n(CC(O)COc3ccc(C(=O)c4ccccc4)cc3)c(=O)n(CC(O)COc3ccc(C(=O)c4ccccc4)cc3)c2=O)cc1]

8. A method of modifying a substrate comprising the step of applying a composition according to claim 1 to the substrate.

9. The method of claim 8, wherein the composition is photoactivated such that at least one photoactivatable group within the composition forms a bond with the surface of the substrate.

* * * * *